US011002722B2

(12) United States Patent
Michael et al.

(10) Patent No.: US 11,002,722 B2
(45) Date of Patent: May 11, 2021

(54) TIME-SERIES GEOCHEMISTRY IN UNCONVENTIONAL PLAYS

(71) Applicant: CONOCOPHILLIPS COMPANY, Houston, TX (US)

(72) Inventors: Gerald E. Michael, Houston, TX (US); Jason Jweda, Houston, TX (US); Yishu Song, Houston, TX (US); Aaron K. Summerfield, Houston, TX (US); Faye Liu, Houston, TX (US); Pipat Likanapaisal, Houston, TX (US)

(73) Assignee: CONOCOPHILLIPS COMPANY, Houston, TX (US)

( * ) Notice: Subject to any disclaimer, the term of this patent is extended or adjusted under 35 U.S.C. 154(b) by 242 days.

(21) Appl. No.: 15/963,757

(22) Filed: Apr. 26, 2018

(65) Prior Publication Data

US 2018/0313807 A1    Nov. 1, 2018

Related U.S. Application Data

(60) Provisional application No. 62/490,180, filed on Apr. 26, 2017.

(51) Int. Cl.
| | |
|---|---|
| *E21B 41/00* | (2006.01) |
| *E21B 43/30* | (2006.01) |
| *E21B 49/02* | (2006.01) |
| *E21B 49/08* | (2006.01) |
| *G01N 30/72* | (2006.01) |

(Continued)

(52) U.S. Cl.
CPC ....... *G01N 33/241* (2013.01); *E21B 41/0092* (2013.01); *E21B 43/30* (2013.01); *E21B 49/02* (2013.01); *E21B 49/08* (2013.01); *G01N 30/7206* (2013.01); *G01N 33/246* (2013.01);
(Continued)

(58) Field of Classification Search
CPC ........... E21B 2049/085; E21B 41/0092; E21B 43/30; E21B 49/02; E21B 49/08; G01N 30/88; G01N 30/7206; G01N 33/241; G01N 33/246; G01V 99/00
See application file for complete search history.

(56) References Cited

U.S. PATENT DOCUMENTS

| | | | |
|---|---|---|---|
| 8,360,143 B2 | 1/2013 | Ziauddin et al. | |
| 8,666,667 B2 | 3/2014 | Michael et al. | |

(Continued)

OTHER PUBLICATIONS

Baskin, David K., et al—"Allocating the Contribution of Oil from the Eagle Ford Formation, the Buda Formation, and the Austin Chalk to Commingled Production from Horizontal Wells in South Texas Using Geochemical Fingerprinting Technology", 2013, AAPG Annual Convention and Exhibition May 2013, 19 pgs.

(Continued)

*Primary Examiner* — Daniel P Stephenson
(74) *Attorney, Agent, or Firm* — Conocophillips Company

(57) ABSTRACT

Method of optimizing well placement in an unconventional reservoir, by obtaining a plurality of produced oil, produced water and produced gas samples from an unconventional reservoir over a period of time, and obtaining a plurality of rock samples from the reservoir. Each of those plurality of samples is chemically fingerprinted, as well as assigned time and location identifiers. This data is then used to generate a plurality of reservoir maps over time and those maps then used to optimizing well placement in the reservoir.

37 Claims, 14 Drawing Sheets

(51) Int. Cl.
G01N 33/24 (2006.01)
G01V 99/00 (2009.01)
*G01N 30/88* (2006.01)

(52) U.S. Cl.
CPC .......... *G01V 99/00* (2013.01); *E21B 49/0875* (2020.05); *G01N 30/88* (2013.01)

(56) References Cited

U.S. PATENT DOCUMENTS

| | | | |
|---|---|---|---|
| 8,781,747 | B2 | 7/2014 | Ziauddin |
| 8,818,736 | B2 | 8/2014 | Nouvelle |
| 9,074,465 | B2 | 7/2015 | Otbivin et al. |
| 2005/0028974 | A1* | 2/2005 | Moody ................. E21B 49/081 166/264 |
| 2010/0307740 | A1 | 12/2010 | Abivin et al. |
| 2013/0138360 | A1 | 5/2013 | Nouvelle |
| 2014/0200810 | A1* | 7/2014 | Zuo .......................... E21B 49/10 702/13 |
| 2015/0300163 | A1* | 10/2015 | Tips ........................ E21B 47/00 73/152.42 |
| 2018/0313807 | A1* | 11/2018 | Michael ............. G01N 30/7206 |
| 2019/0212258 | A1* | 7/2019 | Harrison ................. G01N 30/50 |

OTHER PUBLICATIONS

McCaffrey, Mark A., et al—"Using Biomarkers to Improve Heavy Oil Reservoir Management: An Example From the Cymric Field, Kern County, California", 1996, AAPG Bulletin, vol. 80, Issue No. 6, 16 pgs.

McCaffrey, Mark A., et al—"Oil fingerprinting dramatically reduces production allocation costs", 2012, World Oil, 4 pgs.

McCaffrey, Mark A., et al—Geochemical Allocation of Commingled Oil Production or Commingled Gas Production, 2011, Society of Petroleum Engineers, SPE 144618, 19 pgs.

McCaffrey, Mark A, et al—"Reducing the Cost of Production Allocation by 95% Using a Geochemical Technique", 2006, AAPG Datapages, Online Journal for E&P Geoscientists, Abstract, 1 pg.

Rasdi, Faisal, et al—"An Investigation of Vertical and Lateral Communication in an Unconventional Oil Reservoir Using Geochemistry and Reservoir Simulation", 2012, Society of Petroleum Engineers, SPE 162673, 15 pgs.

Azad, Ali, et al—Accelerating Completions Concept Select in Unconventional Plays Using Diagnostics and Frac Modeling, 2017, Society of Petroleum Engineers, SPE 184867; 13 pgs.

Jweda, Jason, et al—"Optimizing field development strategy using time-lapse geochemistry and production allocation in Eagle Ford", 2017, Unconventional Resources Technology Conference, URTeC 2671245; 17 pgs.

Laughland, Matthew M., et al—"Uncharted Waters: What Can We Learn From Waters Produced From Horizontal Wells in the Permian Basin?", 2014, Unconventional Resources Technology Conference, URTeC 1926712, 9 pgs.

Cipolla, Craig—"How do we optimize hydraulic fracturing in shale resource plays?", 2015, SPE Hydraulic Fracturing Technology Conference, The Woodlands, Texas Feb. 2015; 32 pgs.

Cipolla, C., et al—"Engineering Guide to the Application of Microseismic Interpretations", 2012, Society of Petroleum Engineers, SPE 152165, 24 pgs.

Freeman, C.M., et al—Measurement, Modeling and Diagnostics of Flowing Gas Composition Changes in Shale Gas Wells, 2012, Society of Petroleum Engineers, Spe 153391, 25 pgs.

Nouvelle, Xavier, et al—Novel Method of Production Back-Allocation Using Geochemical Fingerprinting, 2012, Society of Petroleum Engineers, SPE 160812, 14 pgs.

Sandvik, E.I., et al—"Primary migration by bulk hydrocarbon flow", 1990, Organic Geochemistry, vol. 16, Nos. 1-3, 7 pgs.

Langman, Jeff B., Spatial Distribution of 2H and 18O values in the hydrologic cycle of the Nile Basin, 2015, Journal Arid Land, vol. 7, Issue No. 2, 13 pgs.

Bowen, Gabriel J., et al—"Spacial distubution of 18O in meteoric precipitation", 2002, Geology, vol. 30, Issue No. 4, 16 pgs.

Muehlenbachs, Karlis—The oxygen isotopic composition of the oceans, sediments and the seafloor,1998, Chemical Geology, Elsevier, vol. 145, 11 pgs.

Capo, Rosemary, et al—The strontium isotopic evolution of Marcellus Formation produced waters, southwestern Pennsylvania, 2014, International Journal of Coal Geology, Elsevier, 7 pgs.

Chapman, Elizabeth C., et al—Geochemical and Strontium Isotope Characterization of Produced Waters from Marcellus Shale Natural Gas Extraction, 2012, Environmental Science & Technology, vol. 46, 11 pgs.

Frost, Carol D., et al—"Strontium Isotopic Identification of Water-Rock Interaction and Ground Water Mixing", 2004, Ground Water vol. 42, Issue No. 3, 15 pgs.

Ebongue, V. Woule, et al—"Clorine isotope residual salt analysis: A new tool to investigate formation waters from core anayses", 2005, AAPG Bulletin, vol. 89, Issue No. 8, 14 pgs.

Nouvelle, Xavier, et al—"The Malcom distribution analysis method: A consistent guideline for assessing reservoir compartmentalisation from GC fingerprinting", 2010, Organic Geochemistry, vol. 41, 5 pgs.

Bennett, et al—"Oil Fingerprinting for Production Allocation: Exploiting the Natural Variations in Fluid Properties Encountered in Heavy Oil and Oil Sand Reservoirs", 2009, Frontiers & Innovation, CSPG CSEG CWLS Convention; p. 157-160.

Schrynemeeckers—Optimizing Lateral Placement and Production While Minimizing Completion Costs Using Downhole Geochemical Logging, Society of Petroleum Engineers, 2015; p. 1-9.

International Search Report, PCT/US2018/029634, dated Jul. 3, 2018, 2 pgs.

\* cited by examiner

Calculate the Ratios
- R(A)=1.21
- R(B)=0.84
- R(mixture)=1.04

$$A\% = \frac{(R_{mix} - R_B)}{(R_A - R_B)} = \frac{1.04 - 0.84}{1.21 - 0.84} = 52\%$$

$$B\% = 1 - A\% = 48\%$$

TIME-SERIES GEOCHEMISTRY IN UNCONVENTIONAL PLAYS

PRIOR RELATED APPLICATIONS

This application is a non-provisional application which claims benefit under 35 USC § 119(e) to U.S. Provisional Application Ser. No. 62/490,180 filed Apr. 26, 2017, entitled "TIME-SERIES GEOCHEMISTRY IN UNCONVENTIONAL PLAYS," which is incorporated herein in its entirety.

FIELD OF THE DISCLOSURE

The disclosed methods relate generally to the optimal placement of wells in unconventional reservoirs.

BACKGROUND OF THE DISCLOSURE

Geologic formations may contain large quantities of oil or gas, but can have a poor flow rate due to low permeability, or from damage or clogging of the formation during drilling. This is particularly true for tight sands, shales and coalbed methane formations. Hydraulic fracturing (aka fracking) requires the pumping of fluids under high pressure into reservoirs to create fractures in the rock, thus improving flow. Fracking thus stimulates wells drilled into such formations, making profitable what would otherwise be a prohibitively expensive process.

Indeed, the combination of hydraulic fracturing with horizontal drilling has opened up shale deposits across the country and brought large-scale natural gas drilling to new regions. Shale deposits in combination with other unconventional resources such as heavy oil using steam assisted gravity drainage (SAGD) as well as cyclic steam stimulation (CSS) techniques have allowed economic production of a variety of unique reservoirs. Oil reserves that previously were thought commercially unfeasible to access are now being developed, even in the far North and Artic regions. In fact US oil production reached a 47 year high in 2015 (the highest being 1970).

The optimal spacing of horizontal wells in unconventional field developments remains a major uncertainty because of the lack of information regarding the volume of rock being drained, sometimes referred to as drained rock volume (DRV). The drained rock volume is often less than the stimulated rock volume (SRV). If spacing in either the vertical or lateral dimension is too wide between horizontal wells, hydrocarbon resources are left behind, and if too close, wells compete for the same in-place resource. Economic value during unconventional field development may be significantly reduced by sub-optimal horizontal well spacing.

Various methodologies, such as micro-seismic monitoring during the hydraulic fracturing process and monitoring pressure and injected tracers during production, have been used to evaluate wellbore communication and fracture network connectivity. However, these measurements are only proxies for understanding reservoir drainage, but define the stimulated rock volume.

There are a number of proxy solutions aimed at understanding the SRV through utilization of injected tracers in frack fluids, microseismic event distributions, and production metrics and pressure data between wells. These solutions are based on assumptions that may or may not be well understood in the unconventional realm, and rely on rock behavior during completion and production processes. Most importantly, the SRV does not necessarily equate directly to an effective drainage volume due to a variety of factors including possibly inadequate proppant distribution, reservoir damage, reservoir heterogeneity and the like.

Injected tracers are useful for addressing which stages of the completion are contributing to hydraulic fluid flow, but have a limited utility life as the tracer is either absorbed to strata or their concentration depletes over time.

Microseismic event monitoring is a powerful method for determining fracture patterns and densities during hydraulic fracturing processes. These events provide an important glimpse into rock behavior and the spatial extent of fracturing. Unfortunately, there is no straight forward method of determining whether microseismic events equate to amount and degree of hydrocarbon fluid flow. As with injected tracers, microseismic monitoring only provides a snapshot of the initial subsurface environment prior to production.

Pressure monitoring before and during production can be very helpful for determination of connectivity between wells because pressure responses between wells are a measurement of compression wave responses through a porous medium through time. Therefore, pressure monitoring adds a time component to understanding fracture connectivity, but still remains a remote detection method that cannot provide critical information about drained volumes.

Mechanical flow meters or remote sensing derived flow rate or volume are sometimes used to determine which parts of a well are contributing to production; however, neither method actually provides information on how far vertical or lateral from the well bore the fluid flow drainage is being derived. Ultimately, these technologies offer a wealth of information about the SRV and subsurface rock responses to completion and production, but do not directly address effective drainage volume (DRV) per well.

In 2013, Baskin, et al. described the first known application of geochemical fingerprinting technology to a shale-oil reservoir. He studied 18 oil samples produced from wells in South Texas, with the goal to determine if some of the oil produced from horizontal wells completed in one formation contained oil from another nearby reservoir because of the natural or induced fractures that extended therebetween.

This first required Baskin to determine if: (1) oil fingerprinting could differentiate oils produced from different reservoirs; (2) compositional differences could be employed as natural tracers to evaluate vertical communication between the reservoirs; and (3) the amount (if any) of contribution of oil produced in one of the wells from the other reservoir.

His results demonstrated that compositional differences did exist, and he concluded that about 9% of the oil produced from a horizontal well completed in the reservoir was actually from the second play.

What is needed in the art are better methods to quickly, accurately, and inexpensively determine the effective vertical and lateral drained rock volume over time from horizontal wells in an unconventional reservoir. This could then be used to determine production allocation, which can be used in reservoir modeling, to optimize well placement and thereby production of oil and recovery factors.

SUMMARY OF THE DISCLOSURE

The disclosure describes a methodology that allows quantitative production allocation down to intra-formation level, not just between gross formations (e.g. Austin Chalk vs. Eagleford) as demonstrated by in Baskin et al., 2013. By fingerprinting oil, water, and gas samples from the reservoir, and extending fingerprinting over time, the source of produced fluids may be quantitatively allocated to unique production zones.

The effective drainage volume of horizontal wells in unconventional reservoirs can be determined by collecting, analyzing, and interpreting the geochemical signatures contained in produced fluids from those wells. Natural changes in geochemistry of in-situ gas and oil within the reservoir arise from differences in organic matter type, the kerogen kinetics, thermal maturity, hydrocarbon migration and/or local changes in conversion from catalytic effects. These differences in chemistry are often homogenized in conventional reservoirs over geological time from processes of density driven mixing and diffusion as a function of the strata porosity and permeability, strata temperature and pressure and fluid viscosity.

However, in very low permeability reservoirs $<10^{-6}$ md, such as the Eagle Ford and Niobrara shale plays, the homogenization process can take millions of years to occur over lateral distances of only hundreds of feet. Vertical mixing and homogenization can be further slowed by rock strata heterogeneity (i.e., tortuosity; low matrix permeability, inter bedded zones) to the point of setting up discrete chemical signatures vertically. Therefore, the reservoir ultimately may record a significant amount of both vertical and lateral geochemical heterogeneity. This geochemical heterogeneity represents temporal and spatial variability in organic facies, depositional conditions, and thermal maturity across and through the reservoir.

We take advantage of the heterogeneity herein by comparing and linking the geochemical fingerprints of produced fluids to source characteristics of the rock drained in horizontal wells landed in multiple zones within the reservoir. These geochemical fingerprint differences by strata are confirmed from oil samples extracted from vertical core samples. Geochemical signatures are used to determine the distance of drainage from the well-bore and thus determine the drained rock volume.

In one embodiment, production is allocated in a plurality of reservoirs by obtaining rock samples from different zones in the reservoir(s) and chemically fingerprinting extracts from the rock samples; obtaining produced oil, produced water, and produced gas samples from one or more reservoirs over time; chemically fingerprinting the samples to provide oil fingerprints, water fingerprints, and gas fingerprints; assigning a time and location the oil, water, and gas fingerprints; and allocating production from one or more wells in relation to the time and location of the fingerprints.

In another embodiment, well placement is optimized in a reservoir, by obtaining rock samples from different zones of the reservoir(s); chemically fingerprinting extracts from the rock samples to provide rock fingerprints; grouping the zones into unique production zones by determining unique fingerprints; obtaining a plurality of produced oil, produced water and produced gas samples from the reservoir(s) over a period of time; chemically fingerprinting the samples to provide oil fingerprints, water fingerprints, and gas fingerprints; assigning a time and location identifier to each of the oil, water, and gas fingerprints; determining which of the samples originate from which production zone by comparison to the unique fingerprints and determining a level of mixing according to the following equations:

$$p_i = \sum_{j=1}^{m} r_{i,j} w_j \ (i = 1 \ldots n) \ n \geq m$$

-continued $$\sum_{j=1}^{m} w_j = 1 \ 0 \leq w_j \leq 1$$

inputting data from the unique production zones and the level of mixing into a reservoir modeling program; optimizing well placement using the reservoir modeling program; and implementing the optimized well placement in the reservoir(s).

In an additional embodiment, production is allocated in an unconventional reservoir, by: obtaining rock samples from different zones in an unconventional reservoir(s); chemically fingerprinting extracts from the rock samples to provide rock fingerprints; grouping the fingerprints into unique production zones; obtaining produced oil, produced water, and optionally produced gas samples from one or more zones of an unconventional reservoir(s) over time; chemically fingerprinting the samples to provide one or more oil, water, and gas fingerprints; where the fingerprint data is simplified by generating ratios of all possible compound ratios, and selecting a ratio for use if the ratio is generally constant, and each compound in the ratio follows linear mixing rules; determining which portion of the samples originate from which production zone(s) by comparison to the unique fingerprints and determining a level of mixing according to linear algebraic equations, and determining which unique zone contributes to production of oil, gas and water samples and how much.

The fingerprints comprise ratios of compounds that are generally constant between rock samples and produced samples. Each compound in a ratio generally follows linear mixing rules. The raw fingerprinting data may be fed into a macro that builds non-normalized (AB) and normalized (A/A+B) ratios of all possible compound ratios, and then ranks ratios using a square of Pearson correlation, where a ratio is selected for use in the method if the ratio is generally constant between rock samples and produced samples, and each compound in the ratio follows linear mixing rules, and the ratio is clearly separate from drilling mud ratios.

Location information may include depth and lateral placement (x, y and z axes). A reservoir map may be generated in the form of tables including fingerprint data organized by location (x, y and z axes) and time.

Chemical fingerprinting may use GC, MS, GC-MS, FTICR-MS, TLC, 2D TLC, CE, HPLC, FTIR Spectrophotometry, XRF, AAS, ICP-MS, IC, NMR, GCxGC-TOFMS, SARA, CHNOS analysis, elemental analysis, GC/IR-MS, or any combination. In one embodiment, chemically fingerprinting step uses GC-MS. In another embodiment, the ratio of gasoline compounds, biomarkers, gas compositions, water isotopes, and the like may be used. In another embodiment, water fingerprints like chlorine, bromine, strontium, water deuterium, water oxygen, sulfur, iron, and the like may be used. In yet another embodiment, gas fingerprints may include carbon (13), sulfur (34), methane, ethane, propane, butane, pentane, H2S, and the like. Alternatively, fingerprints may include API gravity, elemental composition, saturate levels, aromatic levels, resin levels, and asphaltene levels (SARA) fractions.

In more detail, the invention uses the geochemical fingerprints of produced oil and gas samples from horizontal wells collected over time. Automated generation and screening for the thousands of possible ratios (compounds and isotopes) that provide information by stratigraphic interval is facilitated automated analysis including Microsoft Excel based macros and the like. Compound ratios are screened based on concentration for adherence to linear mixing rules, for consistency between extracted and produced sample, as well as for compounds/ratios whose variance is above analytical variation (Nouvelle and Coutrot, 2010). The basis of quantitative production allocation are matrix linear algebra solutions with modification in order to handle large matrices and explore uncertainty around a non-unique solution (McCaffrey et al., 1996, Nouvelle et al., 2012).

During hydrocarbon production on horizontal wells, produced samples (oil, gas, water) are collected from the high pressure separator (HPS) at regular time intervals. Production details (e.g., daily rates, yields) and wellhead/separator conditions are recorded at the time of sample collection.

Existing or new core samples or drill cuttings can be collected, extracted and analyzed as well. These are used to establish the chemical fingerprints of chemically distinct zones in the reservoir(s), and these end-member fingerprints are used to determine when mixing is occurring, from which zones, and how much.

Samples are collected over time and are intended to capture produced fluid variability at the beginning of production occurring due to initial connectivity between fracture networks. Since fracture connectivity is thought to decrease with reduced pressure as drawdown proceeds and fractures close under the reduced pressure, a slower sampling rate can be used later in well life. Although the rate of sampling may slow, it is beneficial to continue monitoring fluids at a regular interval in order to capture changes in the drainage system and any hydrocarbon phase property variability through time.

Produced fluids can be analyzed for a variety of bulk and geochemical parameters to establish the produced fluid fingerprints. Routine analyses for produced gas samples include gas compositions and carbon (13) isotopes (methane-pentane), as well as $H_2S$ and sulfur (34) isotopes in the case of the Eagle Ford. However, these analyses are exemplary only and many other methods of generating fingerprints could be used.

Bulk oil parameters include API gravity, elemental compositions, and Saturates, Aromatics, Resins, Asphaltenes (SARA) fractions. Detailed oil analyses for composition and biomarkers include whole oil-GC, aromatics-GC-MS, and saturates-GC-MS. The required analytical program may vary between plays and perhaps for different parts of a play, but typically a standard set of analysis in a given region will be used. Further, these particular analyses are exemplary only and other analytical methods can be used to generate fingerprints for the methods of the invention.

The Eagle Ford spacing pilot projects, with multiple horizontal wells in multiple geologic zones, offer a unique opportunity to evaluate effective drainage behavior within a data-rich framework through time. The combination of multiple fluid analyses from producing wells in a spacing pilot project can provide robust and repeatable differences between produced fluids of nearby wells. Linking geochemical signatures found in the produced fluids to particular originating reservoirs or sub-reservoirs is an additionally powerful tool for determining production allocation.

To our knowledge, no other operator or vendor is using time-series reservoir geochemistry in concert with production, microseismic, and tracer data in an unconventional asset to determine effective drainage heights and production allocation. In one embodiment, time-series reservoir geochemistry is analyzed using a spatial mapping on the x, y, and z axes in a known reservoir. Additionally changes over time may be monitored.

There are some major advantages of employing the time-series reservoir geochemistry technology compared to previous methodologies, including injected tracers, microseismic event distribution, pressure monitoring and mechanical flow monitoring.

First, time-series reservoir geochemistry is inexpensive relative to the other methods. Geochemical monitoring of a single well monitoring (depending on the duration and type of analytical program) is approximately $50-80K US/well per year, whereas other methods cost upwards of $50-500K US/well per year.

Second, this type of monitoring is also advantageous in that produced fluid sampling does not burden or delay rig schedules and can be flexible with production maintenance. Thus, it is not inconvenient to deploy the method.

Third, geochemical compositions are fingerprints of the actual produced hydrocarbons. The time-series reservoir geochemistry method is therefore not a remote sensing based technology, but a direct measurement technology. It can thus be used quantitatively in determining vertical and horizontal effective drainage lengths and how it can vary over time.

As used herein a "fingerprint" is an analysis of the chemical and/or isotopic components of a sample and is typically complex enough to uniquely identify the source of oil, gas and water samples. "Fingerprinting" refers to the analyses needed to generate the fingerprints.

The fingerprint data is typically a very large data set, which under current processing limitations, is simplified for use. Herein, we generated ratios of compounds, and selected those ratios that were relatively constant between core and production samples—e.g., the act of producing the samples did not change the data significantly. However, with sufficient processing power, other methods could be used.

Ratios used herein include nonnormalized AB and normalized A/(A+B), (A−B) and may include compound ratios.

As used herein, a "reservoir" is a formation or a portion of a formation that includes sufficient permeability and porosity to hold and transmit fluids, such as hydrocarbons or water or natural gas, and the like.

A reservoir can have a plurality of chemically distinct "zones" therein, particularly in very tight rock, where mixing is almost non-existent.

An "end-member" (also endmember or end member) in mineralogy is a mineral that is at the extreme end of a mineral series in terms of purity. In this context, it refers to oils that originate from completely separate zones and thus are chemically distinct—in other words, no mixing with oil from another zone has occurred.

As used herein, "landing zone" refers to the location where an oil is actually produced from a horizontal well.

As used herein, a "well-interference test" refers to pressure variation with time recorded in observation wells resulting from changes in rates in production or injection wells. In commercially viable reservoirs, it usually takes considerable time for production at one well to measurably affect the pressure at an adjacent well. Consequently, interference testing has been uncommon because of the cost and the difficulty in maintaining fixed flow rates over an extended time period. With the increasing number of permanent gauge installations, interference testing may become more common than in the past.

As used herein, "SARA fractions" refers to the four fractions (%) of crude oil that can be separated, including saturates, aromatics, resins and asphaltenes. SARA quantification is typically performed by IP-143 and ASTM D893-69 standards.

A "core" is a sample of rock in the shape of a cylinder. Taken from the side of a drilled oil or gas well, a core is then dissected into multiple core plugs, or small cylindrical samples measuring about 1 inch in diameter and 3 inches long.

"Drilling cuttings" are the small rock samples generated during drilling and returned with the drilling mud.

By "obtaining" a sample herein we do not necessarily imply contemporaneous sampling procedures as existing samples can be used where available. However, most often, contemporaneous sample collection will be needed, except for core samples, which may already be available.

By generating a reservoir "map" we means that the reservoir is characterized in the three directional axes as well as the fourth time axis, but we do not necessarily imply a graphical representation thereof, as data can be maintained and accessed in many forms, including in tables.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention.

The following abbreviations are used herein:

| ABBREVIATION | TERM |
| --- | --- |
| AAS | Atomic Absorbance Spectrophotometer |
| Bbl | Barrel |
| BVO | bulk volume oil |
| CE | capillary electrophoresis |
| DRV | Drained rock volume |
| EOR | Enhanced Oil Recovery |
| FTICR | Fourier Transform Ion Cyclotron Resonance |
| FTIR | Fourier Transform Infra-Red |
| GC | Gas Chromatography |
| GCxGC-TOFMS | 2D gas Chromatography time-of-flight mass spectrometry |
| GR | Gamma ray |
| HPLC | High Pressure Liquid Chromatography |
| HPS | High pressure separator |
| IC | Ion Chromatography |
| ICP-MS | Inductively Coupled Plasma Mass Spectrometry |
| MB | Middle Bakken |
| MS | Mass Spectrometry |
| MTF | Middle Three Forks |
| NMR | Nuclear Magnetic Resonance |
| SARA | Saturates, Aromatics, Resins, Asphaltenes |
| SRV | Stimulated rock volume |
| TF | Three Forks |
| TLC | thin layer chromatography |
| TLG | Time lapse geochemistry |
| UBS/LBS | Upper and Lower Bakken Shale |
| USGS | US Geological survey |
| UTF | Upper Three Forks |
| XRF | X-ray Fluorescence |
| MPLC | Medium Pressure Liquid Chromatography |

DESCRIPTION OF EMBODIMENTS OF THE DISCLOSURE

Figure 1:
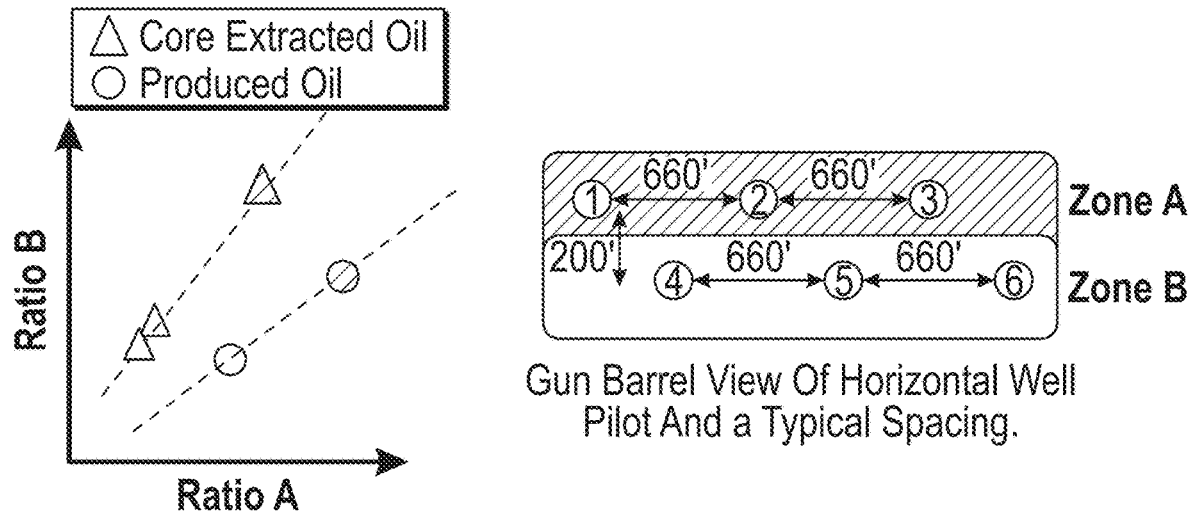
FIG. 1. Example of compound ratios that provide stratigraphic information (separate zone A and B), but are different between extracted oil and produced oil. Ratio A and B could be derived from gas chromatography or gas chromatography-mass spectrometry.

The disclosure provides novel methods of allocating production in an unconventional play, as well as methods using such information, such as optimization well layout in an unconventional play.

Geochemical fingerprinting is possible when the composition of oil in each reservoir, or zones thereof, is different. In that case, when oils produced from discrete zones are commingled, subtle chemical differences in a produced oil sample can be used to assess the contribution from each pay zone. This technique uses high-resolution gas chromatography (GC) data obtained on each oil sample, and also requires the availability of samples of each "end-member" oil that contributes to the production stream. GC peak heights, which reflect the abundance of each compound, can be used to allocate commingled production using linear algebra methods.

Crude oil and oil spill fingerprinting has long been used in the art as a means of identifying oils and/or identifying their sources. However, it has not heretofore been used to allocate production in unconventional plays, or to optimize well placement and spacing.

In more detail, the methodology requires the following:

Collection of samples—Samples are collected over time and include produced oil, gas, water, as well as isotraps for S-isotopes, Draeger tubes for $H_2S$ and $CO_2$, and the like.

Oil, gas and water extracted from core samples or drill cuttings are also used, providing definitive geological placement for particular fingerprints. Some of these samples may already be available, and others can be generated at drilling.

It may be necessary in some cases to subtract injected water fingerprints from produced water fingerprints in order to distinguish in situ (core) water signatures from injected water.

Samples are collected at timed intervals, such as 1 sample/week for the first 3 months, 2 samples/month for the second 3 months, and 1 sample/month for another 6 months. Obviously, these intervals are exemplary only, and sample collection can proceed for years.

Analysis of Samples—the samples are then analyzed by one or more methods to provide accurate fingerprints of the contents. We have exemplified the methods herein using GC-MS, but any methods or combinations of methods can be used, including Gas Chromatography (GC), Mass Spectrometry (MS), GC-MS, thin layer chromatography (TLC), including 2D TLC, capillary electrophoresis (CE), High Pressure Liquid Chromatography (HPLC), Fourier Transform Infra-Red (FTIR) Spectrophotometer, X-ray Fluorescence (XRF), Atomic Absorbance Spectrophotometer (AA or AAS), Inductively Coupled Plasma Mass Spectrometry (ICP-MS), Ion Chromatography (IC), Nuclear Magnetic Resonance (NMR), two-dimensional gas chromatography time-of-flight mass spectrometry (GCxGC-TOFMS), Fourier Transform Ion Cyclotron Resonance mass spectrometry (FTICR-MS), and the like. Additional analysis can include gas compounds, isotopes, bulk oil parameters (API Gv, SARA, CHNOS, elemental), whole oil-GC, aromatics-GCMS (biomarkers), and the like.

Bulk oil analysis methods can also be applied, including e.g., chemical composition, elemental composition, metals, density, specific gravity, API gravity, viscosity, surface tension, interfacial tension, volatility, liquefaction, solidification, carbon residue, Conradson, Ramsbottom, microcarbon, aniline point, specific heat, heat content, enthalpy, PVT relationships, heat of combustion, critical properties, electrical conductivity, dielectric constant, dielectric strength, dielectric loss, power factor, color, refractive index, optical activity, fractional composition, atmospheric distillation, vacuum distillation, solvent treatment, asphaltene separation, fractionation, gas chromatography, simulated distillation, adsorption chromatography, gel permeation chromatography, ion-exchange chromatography, high-performance liquid chromatography, supercritical fluid chromatography, thin layer chromatography, structural group analysis, molecular weight, mixed aniline point, correlative methods, evaporation rate, flash point, Kauri-butanol value, odor, color, volatility, storage stability, thermal stability, sediment, and the like.

In many cases, it may be necessary to separate the samples into two or more fractions before submitting sub-fractions to fingerprinting analysis, because oil components can range from C1 to >C40 in some polyaromatic hydrocarbons, and because there are instances where certain components can interfere with a particular analysis. However, fingerprinting and chemical analyses are well known in oil and gas development, and the person of ordinary skill knows how to apply a correct methodology.

Data Consistency: Fingerprint data can have considerably variability depending on the machines used, operator technique, method of sample collection, storage conditions, age of samples, and the like. Therefore, steps should be taken to ensure internal consistency such that the data is more reliable, including e.g., comparing multiple phases (gases, low and high molecular wt. oil fractions), establishing a standardized protocol for sample collection with single vendor, immediate sample analysis on arrival to minimize aging errors or the use of suitable verified storage conditions, and of course, running external standards and duplicating fluid analyses.

In addition, oils and gases can be analyzed at different laboratories and on different instruments for the same wells. By comparing data from different labs and different machines, a margin if error can be established., and if needed stable datapoints can be selected for use in the subsequent analysis and highly variable data elements omitted.

Data Analysis: Data from a comprehensive fingerprint is very dense and can be difficult to analyze as is. Therefore, some simplifications are undergone to reduce the dataset to a meaningful, yet simpler base with which to work. We used an excel spreadsheet to generate and screen for the thousands of possible ratios (compounds and isotopes) that provide information by stratigraphic interval, are above analytical variation and obey linear mixing rules. These ratios are then used in mapping and production planning.

Sample Collection and Analysis

All samples collected are labeled as to type and also time of collection and precise location. This data is then used in data analysis.

Time-lapse samples typically collected in conjunction are produced oil, gas and water at the separator. The time period over which the sample collection occurs is variable based on the objective and local geology. In general, collection is more frequent in the flowback times (<1 mo.) and tails off with data sets in the ~26 sample range per 6-12 mo. period. This allows the ability to monitor the dynamic nature of drainage heights over time and monitor for other changes in flow behavior (e.g. break out of 2-phase flow) and communication between wells. Collection of samples prior to and after shut-ins for operations or production rate sharing tests also allows for an opportunity to monitor dynamic changes in drainage.

The location of sample collection is prioritized in the order of vertical stacking pilots, next lateral spacing pilots, and least information for one off wells.

All produced water samples are collected in transfer containers prior to processing into sample containers for the laboratory. Samples are processed by transferring the collected sample from the transfer containers to appropriate sample containers for laboratory analyses using a peristaltic pump. Precleaned, one-gallon plastic containers were used as the transfer containers.

The methodology used herein refers to the use of either quantitative concentration (ppm) data or ratios calculated from concentrations derived from peak areas correlated to internal quantitative standards using gas chromatography (GC) or gas chromatography-mass spectrometry (GC-MS). The use of reference samples as external standards, coupled with internal standards allows for tracking of potential drift in the instrumentation or methodology through time and ability to correct without large scale rerunning of samples. In some embodiments, a standard compound or compounds are added to a sample during measurement to provide a known concentration and size marker.

Whole rock core pieces were extracted and the extract processed for chemical composition separation (SARA). The maltenes (saturate, aromatic and resins) were separated by medium pressure liquid chromatography (MPLC). The saturate, aromatic and resins were weighed and then volumetrically diluted for analysis by GC and GC-MS. The chemical finderprints of these rock samples, available from precise depth and lateral locations allows the user to assign distinct geochemical fingerprints to each zone or end-member. If two samples have nearly identical fingerprints, they are from the same end-member.

Chemical and isotopic analyses of constituents dissolved in the water samples were also conducted. Dissolved metals were analyzed using inductively coupled plasma emission spectrometry and mass spectrometry (ICPES, ICPMS), anions were measured by ion chromatography (IC), and pH, temperature, filtration, and preservation were procedures conducted at the well site. Stable isotopic analyses of key indicator constituents were measured by mass spectrometry.

Data Processing

There are two main problems to be solved with production allocation in unconventional tight reservoirs that are solved in this patent. 1) end member signals are problematic due to fractionation between the in-situ reservoir fluid and the produced fluid and 2) the chemical signal of end-members is not a discrete function, but a continuous function (e.g. a gradient in the case of shale plays).

Problem #1 solution. End-member chemical signals are determined from extracted oils using interior core parts. These extracted oil chemical signals do not necessarily correlate with produced oil due to fractionation of compounds during production. Compound fractionation is not restricted to low permeability reservoirs, but has even been observed for higher permeability conventional reservoirs (Sandvik and Mercer, 1990).

Prior attempts to minimize or circumvent the fractionation differences between in-situ and produced fluid in the E&P industry have been tried with the use of extensive preservation (e.g. dry ice and sealing samples at rig site) and/or variable sequential extraction methods in the lab. These methods, while helpful, have serious shortfalls including: a) control of the rig site samples is not always easy or possible, b) sequential extraction methods are likely to be different or change for different rock types and mineralogy, and c) it is time consuming and expensive to derive the correct extraction method.

We propose herein a new method to solve this problem. We assume that there are hundreds or thousands of chemical compounds that do not fractionate during production, e.g., they remaining largely unchanged when brought to the surface. An example could be isomers of the same compound (e.g. 1 versus 9 methylphenanthrene), which should behave very similarly between in-situ and produced oil. The challenge is find those compounds that are not fractionated between in-situ and produced oils. At the same time, these compounds and compound ratios must carry information in the vertical stratigraphic (age) domain. It is very common to find compounds that carry stratigraphic information but do not pass the screen test for fractionation (FIG. 1). These compounds can still be useful in a qualitative sense for pilot monitoring but do not allow for quantitative production allocation, which are used to derive information on vertical drainage height.

To derive compounds and subsequent ratios that are similar between extracted oil and produced oil, we use a purpose built excel visual basic macro capable of handling large data sets of extracted oils, produced oils and compounds. The macro automatically builds non-normalized (AB) and normalized (A/A+B) ratios of all possible ratios from the compound data supplied. The ratios are ranked according to Pearson product correlation coefficients against an alpha numeric target variable. In practice, since the acceptable correlation could be either strongly positive or negative, the ranking is conducted by using square of Pearson correlation, in place of Pearson correlation.

Pearson correlation:

$$\rho_{BR_i\alpha} = \frac{\sum_{j=1}^{m}\left(r_{i,j} - \frac{1}{m}\sum_{k=1}^{m}r_{i,k}\right)\left(\alpha_j - \frac{1}{m}\sum_{k=1}^{m}\alpha_k\right)}{\sqrt{\sum_{j=1}^{m}\left(r_{i,j} - \frac{1}{m}\sum_{k=1}^{m}r_{i,k}\right)^2}\sqrt{\sum_{j=1}^{m}\left(\alpha_j - \frac{1}{m}\sum_{k=1}^{m}\alpha_k\right)^2}}$$

Figure 2:
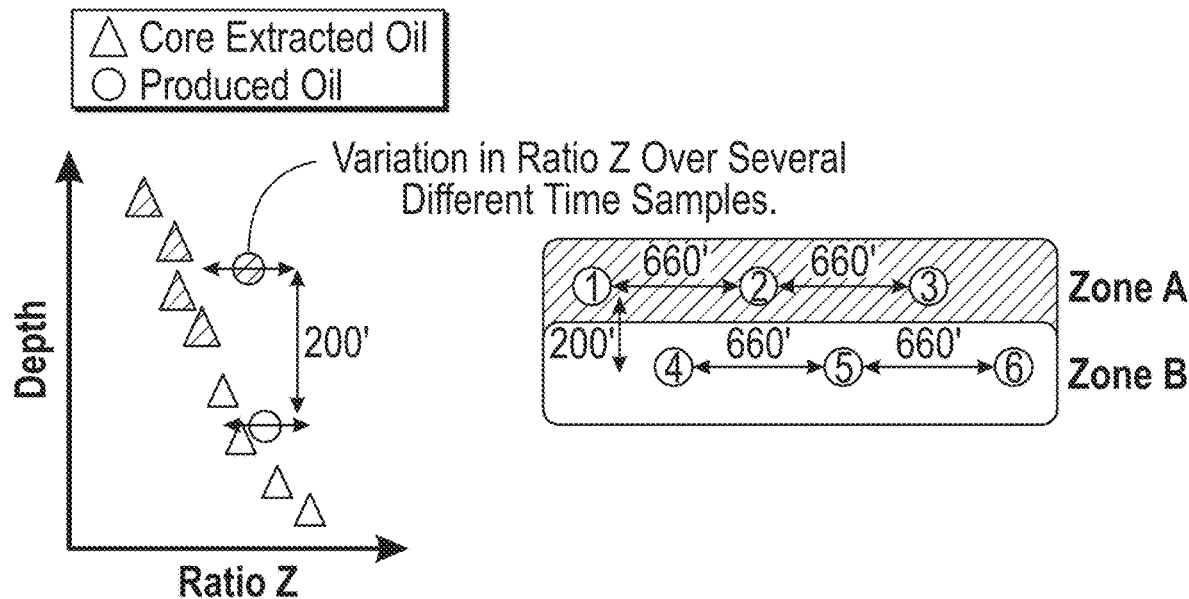
FIG. 2. Example of ratios found that are common for extracted and produced oils, and carry stratigraphic information. The dynamic range of the ratio in the produced oil falls within the range of that from the extracted oil end members.

In production allocation for unconventional reservoirs, the target variable typically confers vertical or stratigraphic distance and is either the actual core measured depth, true vertical depth, or may be grouped by zone. In addition, in order to find ratios that are consistent between the extracted oil and produced oil, this process is performed on a combined extracted oil (from core samples) and produced oil data set. The produced oil is coded in the alpha numeric array closest to the zone of well landing that corresponds to the equivalent depth in the core extracted oil (FIG. 2).

Horizontal well production will be a vertical mixture of produced fluid composite over the whole well length. However, for tight reservoirs it is reasonable to assume that most of the oil produced is proximal to the target landing zone. Having produced oil from multiple zones helps to seed the search for common ratios. The result is that out of thousands of possible chemical ratios there will start to sort out some ratios that provide both vertical stratigraphic information and are in the same dynamic range for produced and extracted oils (FIG. 2).

The ratios found in this manner are still not completely ready for the next step of production allocation. The ratios must be screened to ensure that the dynamic range of the production is never outside that of the potential end-member solution extracted oils.

The next screening step is for the relative concentration of the compounds that constitute the ratios. The mathematical solutions used for production allocation will assume linear mixing rules, which will not be valid if concentration differences are significant among the end members. Ideally, we would want the concentration differences to be zero, but in practice, small differences in concentration can be tolerated with some acceptance of error in solution. For example, concentration differences of up to a factor of 2 difference between end members will still result in <5% error in the allocation solution. In practice, large compound concentration differences over the section of allocation are not typically a problem in liquid rich shale plays, but may become significant in hybrid plays. For most projects, we use ratios that have concentration differences less than a factor of 2.5 between compounds.

Figure 3:
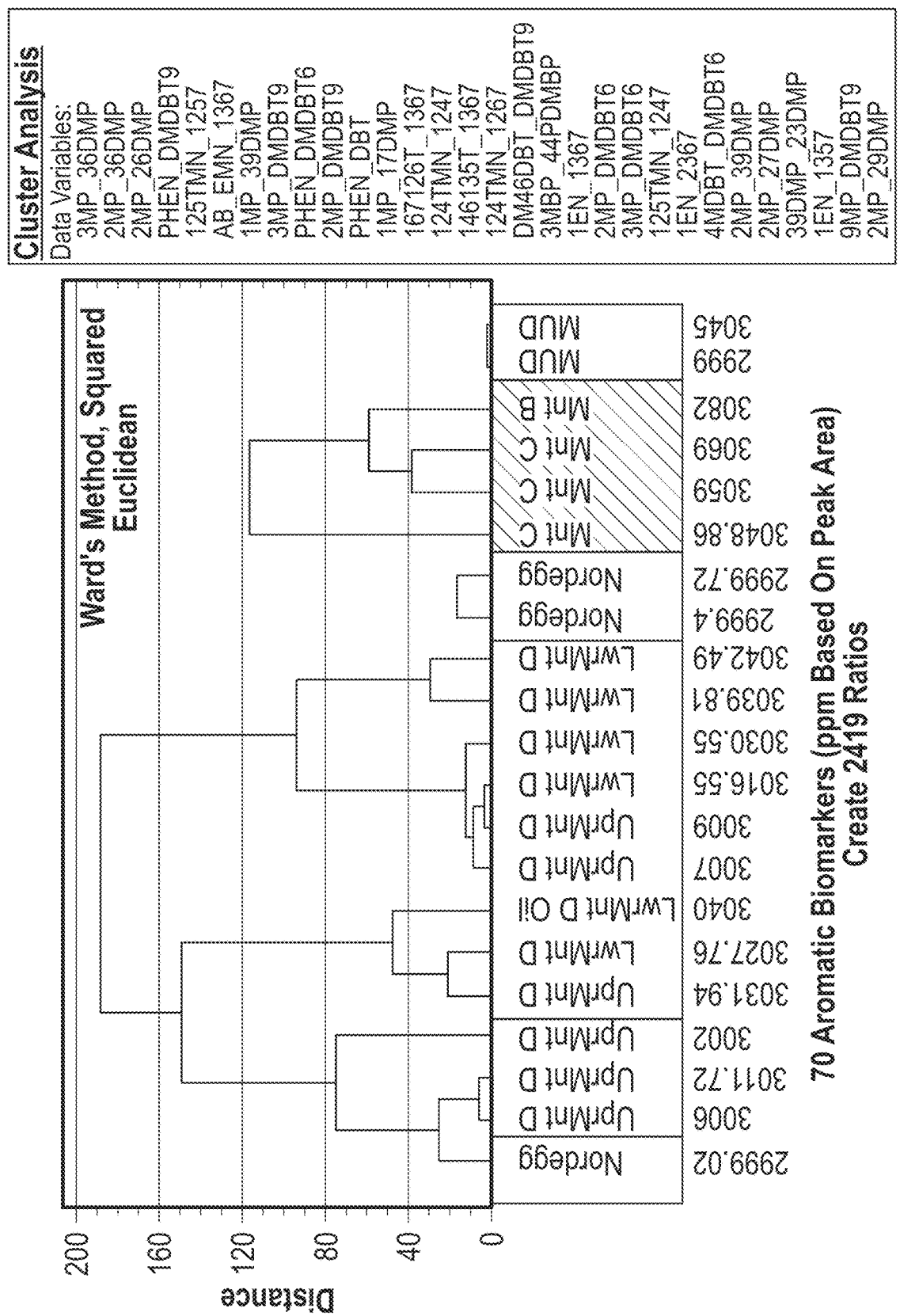
FIG. 3. Example of using hierarchical cluster analysis (HCA) on a set of common ratios for produced oil and extracted oil with stratigraphic information. The groupings show qualitatively the main contributors to the oil sample from a horizontal lateral. The HCA also shows that the common ratios used are clearly separate from the drilling mud as potential contaminate.

If there is any indication that the samples used for end-member derivation could be contaminated by drilling fluids, then the process above is repeated running the numerical array with the macro where drilling mud compounds are included but not coded in the array. The ratios are then checked for correlation with the drilling mud, most commonly by using hierarchical cluster analysis (FIG. 3). If the top ranking common ratios for produced oil and extracted oil do not easily separate out from the drilling mud, then the ratio data needs to be sorted for non-mud validity. This sorting can often be done using the excel macro and re-coding the target variable between the drilling mud and the already high-graded common ratio set that contains stratigraphic information.

The main workflow for ratio generation, selection and screening is summarized in Table 1. Another screening that may be applied involves analytical error of measurement from the GC or GC-MS data for the selected ratios. This is commonly addressed by measuring external standards and determining the error bar for selected ratios and using a constant instrument for the life of the allocation project.

TABLE 1

Summary of ratio selection and screening prior to performing quantitative production allocation.

| Pearson product correlation | Contamination with drilling fluids or other | Dynamic range | Concentration difference check |
|---|---|---|---|
| Select highest relationship by stratigraphy, common to extracted and produced oil | Ratios can see around the mud or other contaminates | Produced oil ratios are in the same range as core extract oil | Up to 4 to 1 is about an 8% error |

Figure 4:
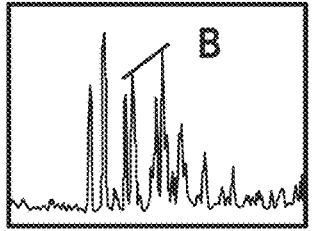
FIG. 4. Example of a discrete end-member matrix with two end-members. The concentrations of the compounds in this example are similar and mix in a linear manner as proven by the physical lab mixture.
Figure 4:
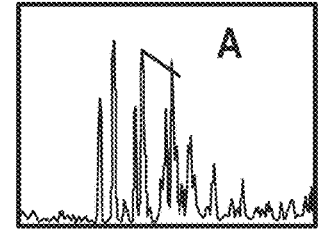
Figure 4:
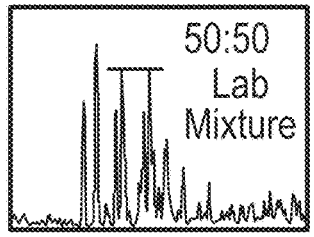
Figure 5:
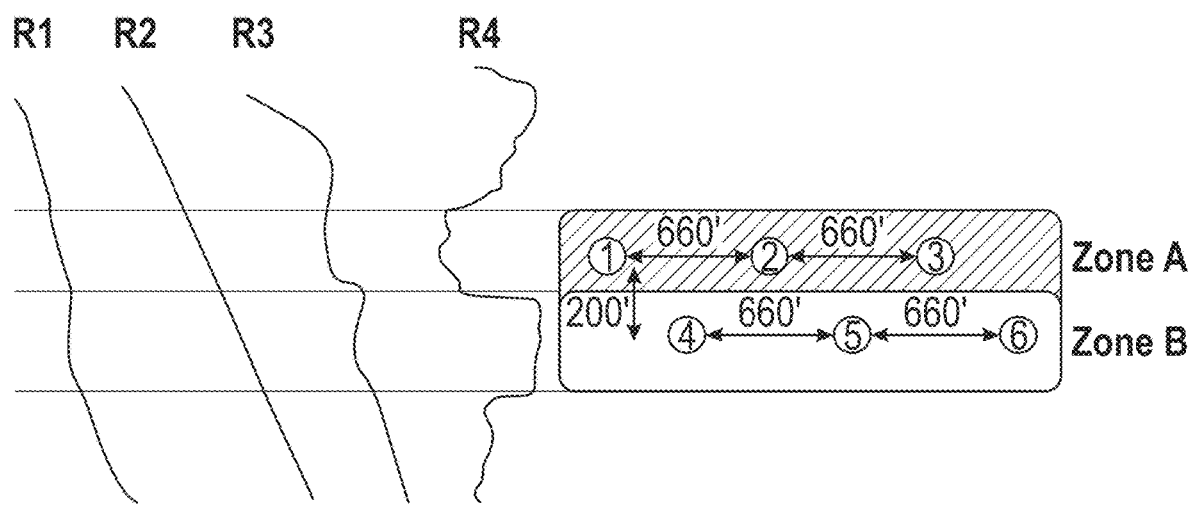
FIG. 5. Example of multiple ratios R1 . . . Rn that have different resolution or separating capacity with depth.

Problem #2 solution. In a discrete end-member solution problem, the production allocation solution can be unique given more or equal ratios than end-members (Nouvelle et al., 2012, 2011) (FIG. 4).

In the case of unconventional tight reservoir production allocation, the end-members often form a continuous gradient (positive or negative) with depth in the case of liquid rich shale plays to multiple gradients in the case of hybrid plays. In either case, some ratios may provide a high degree of separation information over only a selected depth range, but provide no information over other depth ranges. The solution is to incorporate multiple ratios over the allocation depth range and solve simultaneously to an objective function such as minimum least-square $\Sigma(x1-x0)2$.

The matrix linear algebra solution used is shown schematically below.

| Matrix Solution: Linear Algebra R*W = P | | | | | | | |
|---|---|---|---|---|---|---|---|
| | End Member Biomarker Ratio (R) | | | × | Production Allocation (W) | = | Produced Oil Biomarker Ratio (P) |
| | $EM_1$ | $EM_2$ | ... | $EM_m$ | $w_1$ | | $p_1$ |
| BR1 | $r_{1,1}$ | $r_{1,2}$ | ... | $r_{1,m}$ | $w_2$ | | $p_2$ |
| BR2 | $r_{2,1}$ | $r_{2,2}$ | ... | $r_{2,m}$ | ... | | $p_3$ |
| BR3 | $r_{3,1}$ | $r_{3,2}$ | ... | $r_{3,m}$ | $w_m$ | | ... |
| ... | ... | ... | ... | ... | | | $p_n$ |
| BRn | $r_{n,1}$ | $r_{n,2}$ | ... | $r_{n,m}$ | | | |

$$p_i = \sum_{j=1}^{m} r_{i,j} w_j (i = 1 \ldots n) n \geq m$$

$$\sum_{j=1}^{m} w_j = 1 \quad 0 \leq w_j \leq 1$$

System: R × W = P
Constraint: $w_j \geq 0$ for $j \in \{1, \ldots, m\}$
Algorithm:

1. Initialize $w_j = \frac{1}{m}$ for $j \in \{1, \ldots, m-1\}$, or by random sampling 2. Set up Excel solver to minimize mismatch function by controlling $w_j$ for $j \in \{1, \ldots, -1\}$ with the constraint -continued

| Matrix Solution: Linear Algebra R*W = P | | | | |
|---|---|---|---|---|
| End Member Biomarker Ratio (R) | × | Production Allocation (W) | = | Produced Oil Biomarker Ratio (P) |

3. Calculate $w_m = 1 - \sum_{j=1}^{m-1} w_j$, directly embedding $\sum_{j=1}^{m} w_j = 1$ into the workflow 4. Predict produced biomarker ratio based on the system equation, P = R × W 5. Calculate mismatch function, e.g., $\sum_{i=1}^{n} (p_i^{produced} - p_i^{predicted})^2$ 6. Check for convergence
    a. If convergence is failed, based on the mismatch function and previous iterations, Excel solver suggests a new set of $w_j$ for $j \in \{1, \ldots, m-1\}$; then, repeat Steps 2 – 6
    b. If convergence is achieved, stop Depending on the characteristics of the data, different mismatch functions yield different algorithmic behavior and consequently different solutions. In this development, several mismatch functions are included to handle a wide range of problems.

Available mismatch functions:
Least square, $\Sigma_{i=1}^{n}(p_i^{produced} - p_i^{predicted})^2$
Least square with normalization, $$\frac{\Sigma_{i=1}^{n}(p_i^{produced} - p_i^{predicted})^2}{\Sigma_{i=1}^{n}(p_i^{produced})^2}$$

Least square with range correction, $$\Sigma_{i=1}^{n}\left(\frac{p_i^{produced} - p_i^{predicted}}{p_i^{produced}}\right)^2$$

Cauchy, $\Sigma_{i=1}^{n}(1+0.5(p_i^{produced} - p_i^{predicted})^2)$
Cauchy with range correction, $$\Sigma_{i=1}^{n}\left(1 + 0.5\left(\frac{p_i^{produced} - p_i^{predicted}}{p_i^{produced}}\right)^2\right)$$

Range corrected absolute difference, $$\Sigma_{i=1}^{n} \frac{|p_i^{produced} - p_i^{predicted}|}{|p_i^{produced}|}$$

Sensitivity Analyses. As stated in "Problem #2 solution", a larger number of biomarker ratios than the number of end-members are necessary to accommodate the continuous gradient nature of the ratios in an unconventional tight reservoir. To efficiently determine an appropriate number of biomarker ratios, in this development, the sensitivity test can be facilitated in both automatic and manual fashions.

In addition, the choice of end-members can have impacts on the calculated production allocation as well. For the experts to investigate this sensitivity, the development can generate all possible permutations among all end-members for the calculation, with optional controls—the range of numbers of end-members, filtering for only combinations with certain landing zones, and whether skipping end-members is allowed. Landing zone in this context refers to the horizon in which the horizontal lateral was landed. Landing zone specification and end-member forcing are methods to introduced geologic control and influence on the solutions.

Exploring Alternative Solutions. In the sensitivity analyses, one may arrive at multiple solutions based on different selections of biomarker ratios and end-members. However, those solutions do not represent the uncertainty, associated with the measured quantities—both core extract data and produced samples.

To quantify the uncertainty in the calculated production allocation, after the determination of appropriate sets of biomarker ratios and end-members, multiple realizations of core extract data and produced samples can be generated based on their associated measurement errors. This uncertainty quantification is classified as a Monte Carlo Simulation method.

An extra iteration loop is applied to the presented algorithm to generate realizations of production allocation. In each iteration, the end-member biomarker ratios (r_(i,j)) and the produced biomarker ratios (p_i) are replaced by realization k of the quantities (r_(i,j)^k and p_i^k) that are randomly uniformly sampled from $$r_{i,j}^k \in [r_{i,j}(1-\varepsilon_{end-member}), r_{i,j}(1+\varepsilon_{end-member})].$$

and i $p_i^k \in [p_i(1-\varepsilon_{produced}), p_i(1+\varepsilon_{produced})]$, respectively. Then, the associated uncertainty of the production allocation, can be represented by the ensemble of solutions with a large enough number of realizations.

During each iteration, the mismatch function is based on the difference between p_i^(k,produced) and p_i^(k,predicted). However, the presented outcomes in this development are based on p_i^produced and p_i^(k,predicted). This is so that the realizations can be compared among one another as the presented mismatch values have the same reference, p_i^produced.

Case Study

Figure 6:
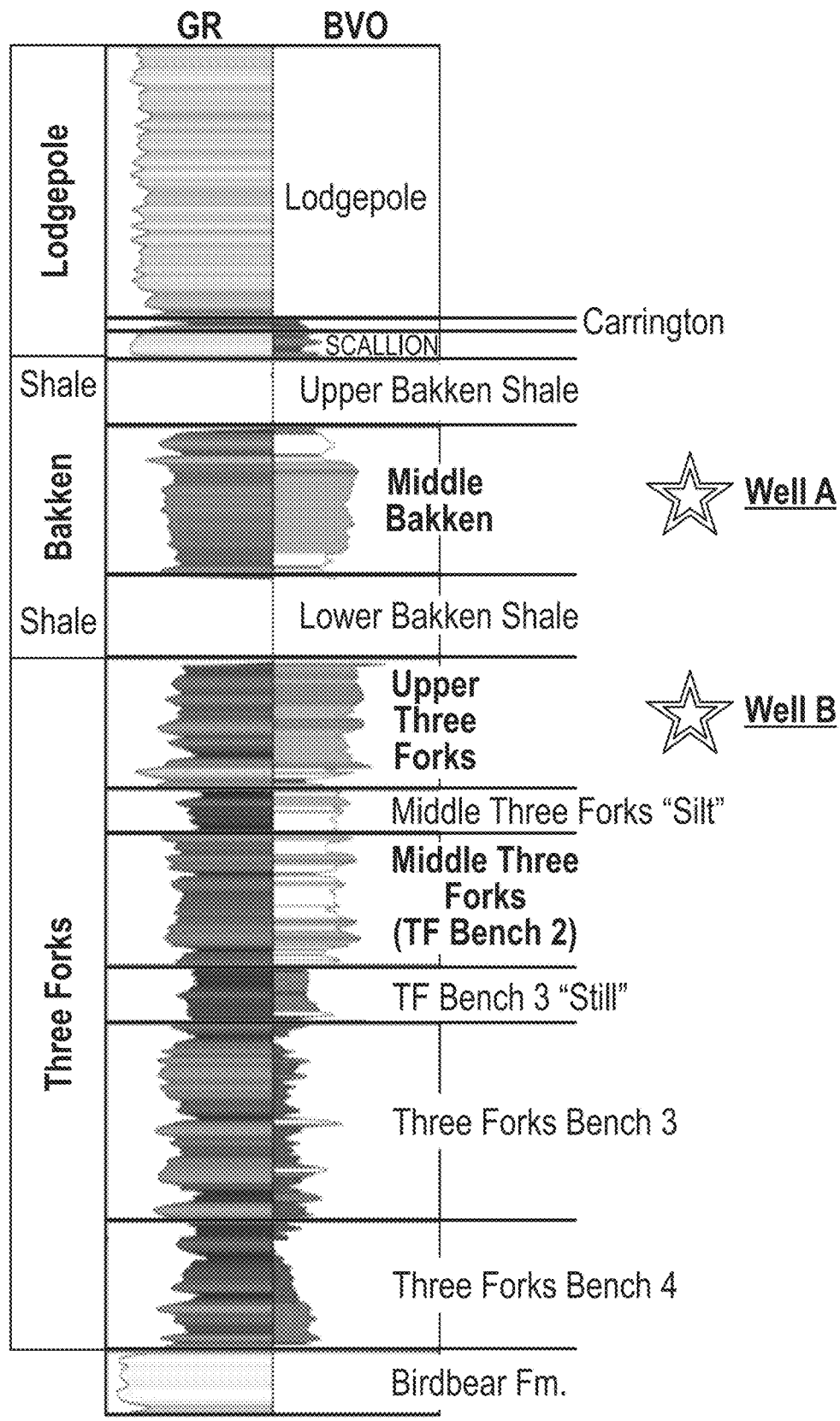
FIG. 6: Well log from the Pilot-hole Well C with associated core gamma ray (GR) and bulk volume oil (BVO) with illustration showing the location of the two horizontal TLG wells (Well A and Well B).
Figure 7:
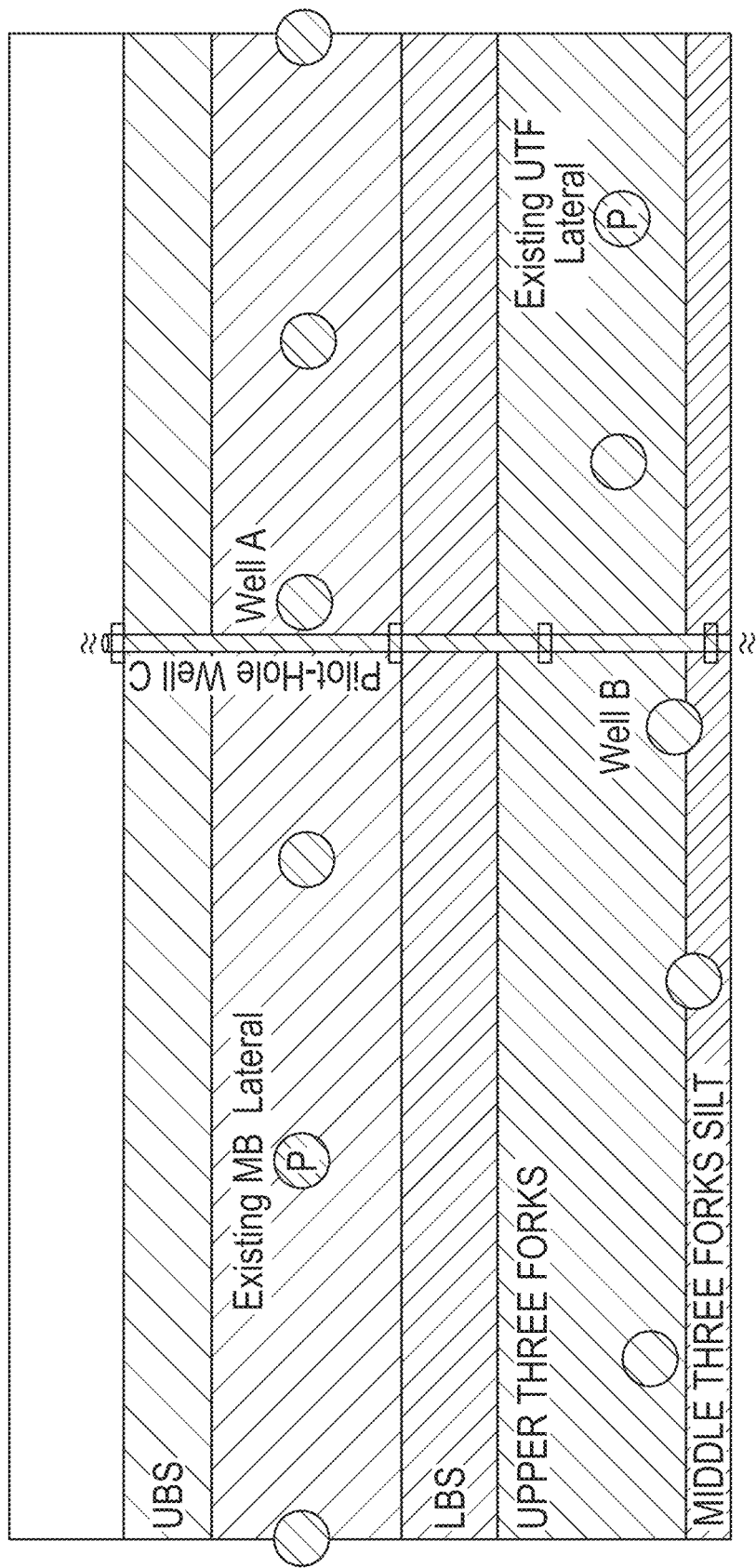
FIG. 7: Cross-section showing locations of the Pilot-hole Well C where the core sample was taken, and the two TLG wells (Well A and Well B). Not to scale.

The Williston Basin is an intracrationic basin with its center in North Dakota. There are two major formations of hydrocarbon production in the Williston Basin—the Late Devonian-Early Mississippian age Bakken Formation, and the underlying Devonian Three Forks Formation. The 2013 USGS assessed an undiscovered, technically recoverable resource estimate of the Bakken Formation at 3.65 billion bbl and the Three Forks at 3.73 billion bbl. The study area is located in the McKenzie County, adjacent to the Nesson Anticline, which is considered the sweetspot of the basin For this study, end-member oil samples (samples of oil from each of the different production zones being commingled) were extracted from the interior pieces of a fresh preserved core from a pilot-hole well (Well C). A number of oil extracts were selected from the stratigraphic zones of interest. A full year of produced oil, gas and water sampling starting from flow-back was launched on two wells from the Middle Bakken and Upper Three Forks (FIG. 6-7) that were in close proximity to where the core was taken. Samples were taken at 12-hour interval during flowback and spaced out at 2-month intervals at the end.

Four producing end-members were identified from core extracts and used in this study, namely, the Upper and Lower Bakken Shale (UBS/LBS), Middle Bakken (MB), Upper Three Forks (UTF), and the Middle Three Forks (MTF). The Upper and Lower Bakken Shales were indistinguishable in terms of their chemical composition, and they are therefore lumped into one end-member. Other surrounding intervals were considered only marginally productive and were not included in this study.

Whole oil gas-chromatography (GC), API gravity, and gas-chromatography mass-spectrometry (GC-MS) on the saturates and aromatics were conducted on the core extracts and produced oils. All the data processing and calculation were conducted using an Excel based software package.

For the current study, it was decided that the GC-MS on the aromatic fractions carried the most effective information on the vertical zone differentiation, and these were therefore used for the quantitative production allocation reported herein.

Figure 8:
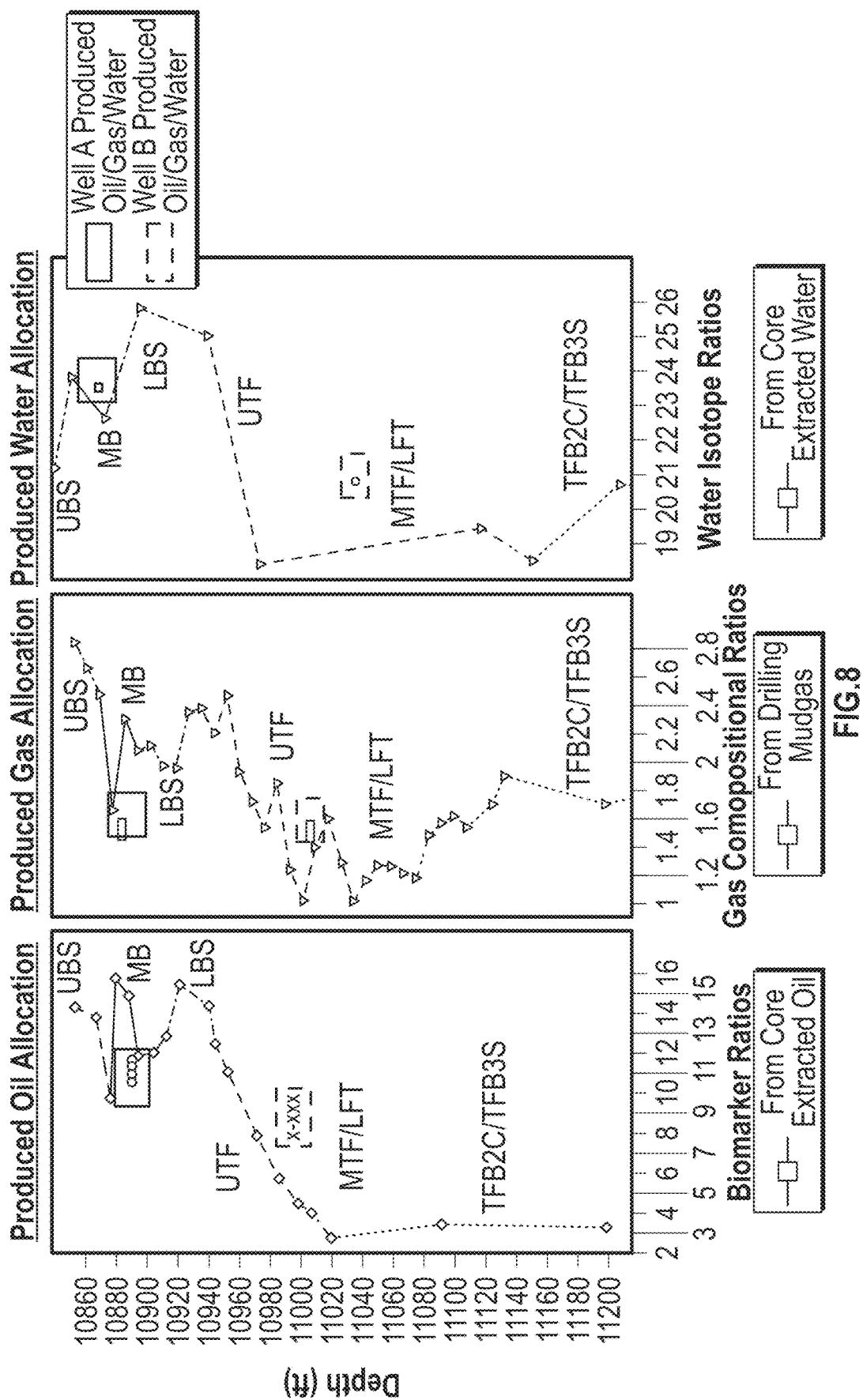
FIG. 8: Cross-plot of chemical signatures vs. depth in end-members vs. produced fluid of oil, gas, and water respectively.
Figure 9:
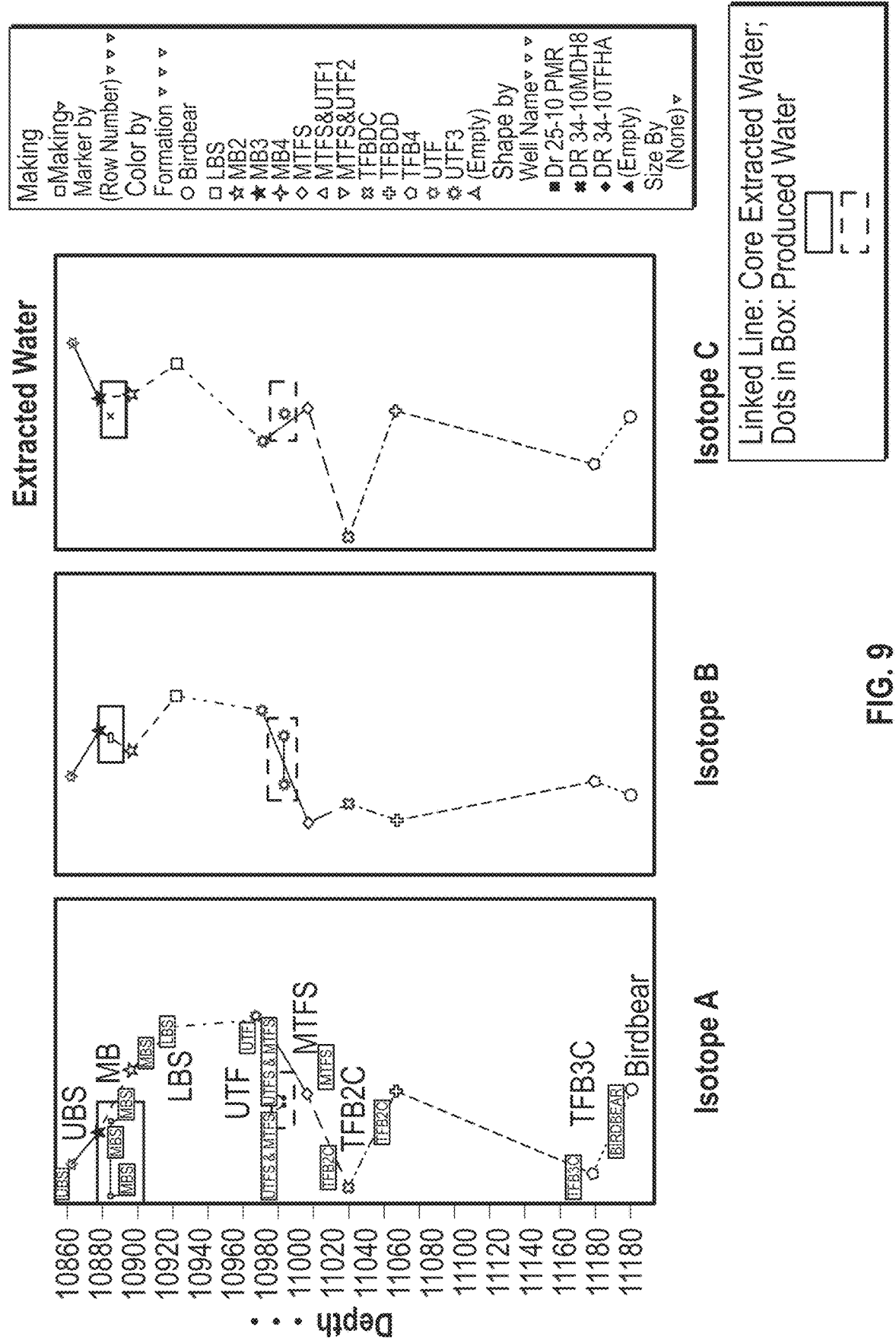
FIG. 9: Cross-plot of chemical signatures vs. depth in end-member water compared to produced water.

In the current case study, oil and water geochemistry were found to be most useful for performing quantitative production allocation by interval (FIG. 8). By contrast, the ability to establish end-members for gas composition with only drilling mudgas composition for comparison was insufficient for quantitative calculation, although trends clearly existed that were qualitatively consistent with both the oil and water chemistry. Similarly, water chemistry could be used to qualitatively assist with the allocation, but a quantitative allocation using only water chemistry would be challenging due to a limited number of available isotopes (FIG. 9).

Thus, oil and water are used, or oil, water and gas can be used to establish distinct reservoir zones (end-members) and their geochemical fingerprints. This data is used to determine when produced samples from the distinct zones have been mixed and in what ratios.

Figure 10:
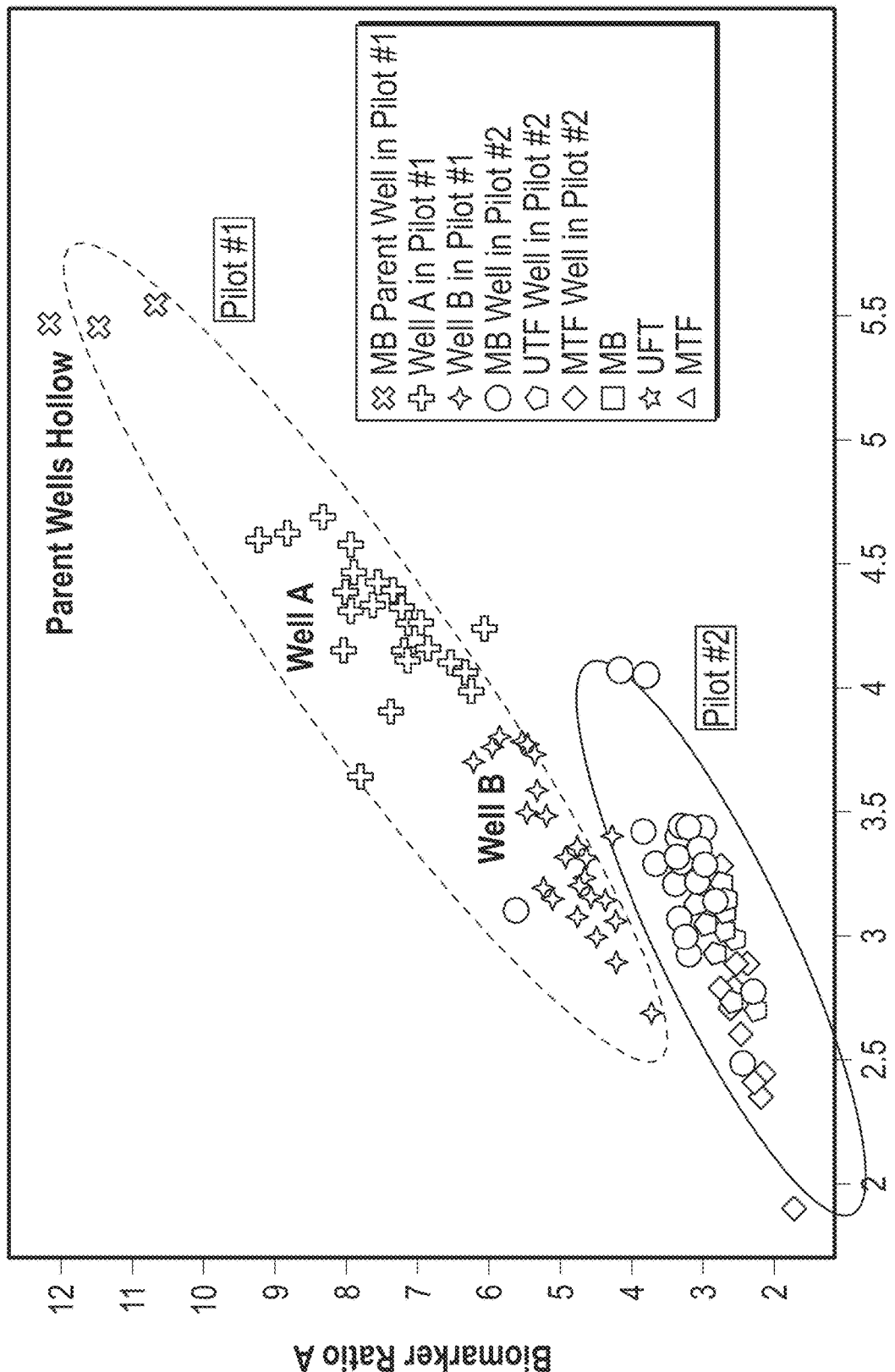
FIG. 10: Separation between MB and TF intervals using two biomarker ratios in produced oil samples from Pilot 1 and 2 areas. Pilot 1 and 2 areas are about 6 miles apart.

In this study, a strong cross contribution was shown between the MB and TF wells, which appeared to continue over the length of one year (FIG. 10). Over the first of production, the MB producer Well A produced ~55% from the MB interval while the UTF contributed ~40%. The TF producer Well B produced ~62% from the UTF while MB contributed ~32%. Shale contribution remained under ~5% in the first year in both wells.

Figure 11:
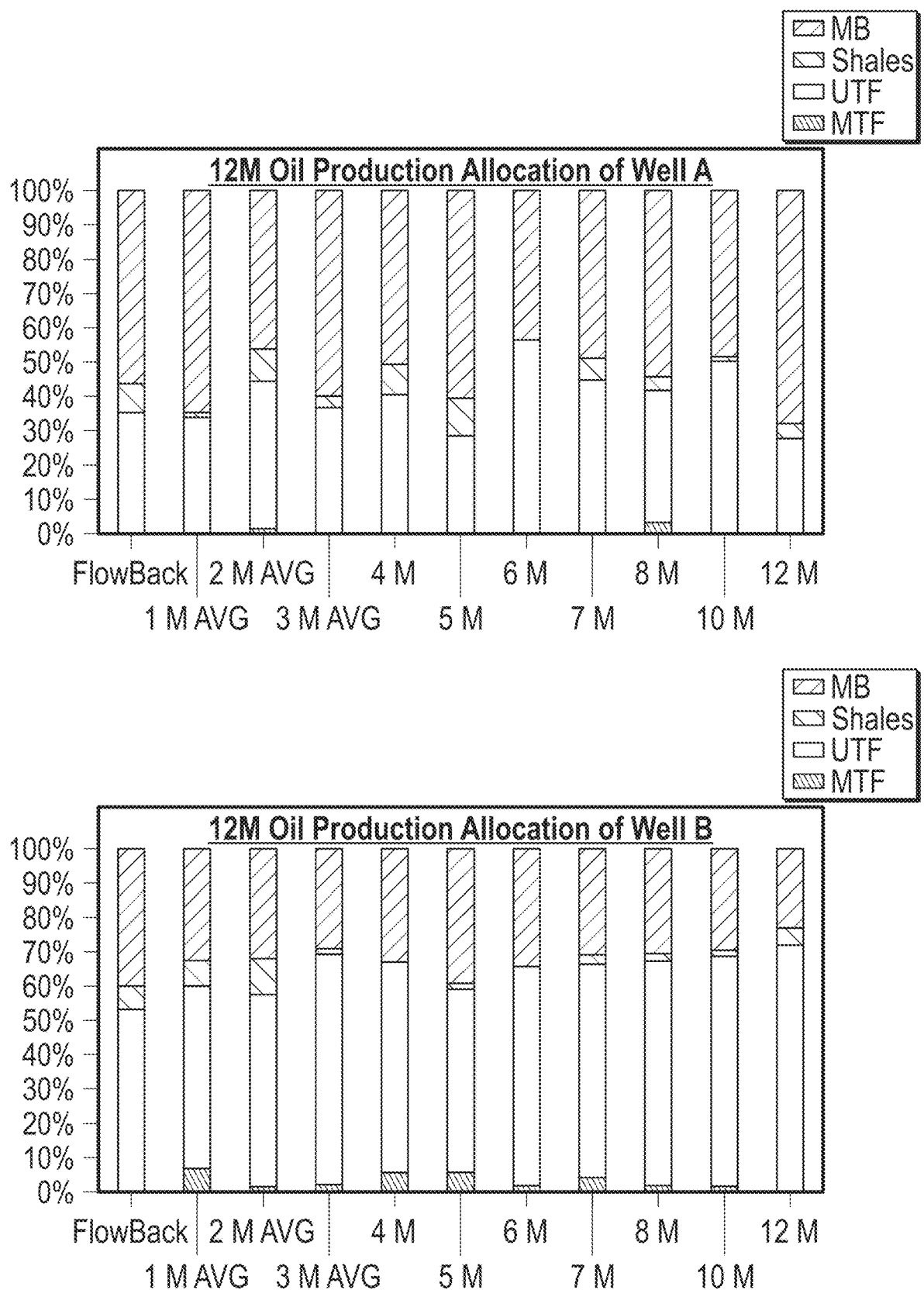
FIG. 11: 12-month production allocation results of the produced oil from Well A (MB well) and B (TF well).

Despite large volumes of in-place oil in the UBS and LBS, their contribution was found to be minimal and close to our error bar of ~±5% on the methodology. The shale contribution did appear to be slightly higher at initial flow back time relative to long term production (FIG. 11 and Table 2). The low amount of shale contribution is consistent with the order of magnitude higher permeability in MB and TF reservoir intervals compared to the shales.

The TLG data support a preferential fracture growth upward in UTF wells and downward in MB for the completion design applied in the pilot. The TLG supported the idea that fractures through the LBS are remaining propped open to flow for both MB and UTF producers up to 1 yr.

TABLE 2

Quantitative allocation results of the produced oil from Well A (MB well) and B (TF well) in 12-month period.

| | Flow-back | 0-6 M Avg. | 7-12 Avg. | Full Year Avg. |
|---|---|---|---|---|
| 12 Month Oil Production Allocation of Well A | | | | |
| UBS/LBS | 9% | 6% | 4% | 5% |
| MB | 56% | 54% | 55% | 55% |
| UTF | 35% | 40% | 40% | 40% |
| MTF | | | 1% | |
| 12 Month Oil Production Allocation of Well B | | | | |
| UBS/LBS | 7% | 4% | 3% | 3% |
| MB | 40% | 34% | 29% | 32% |
| UTF | 53% | 59% | 66% | 62% |
| MTF | | 4% | 2% | 3% |

Figure 12:
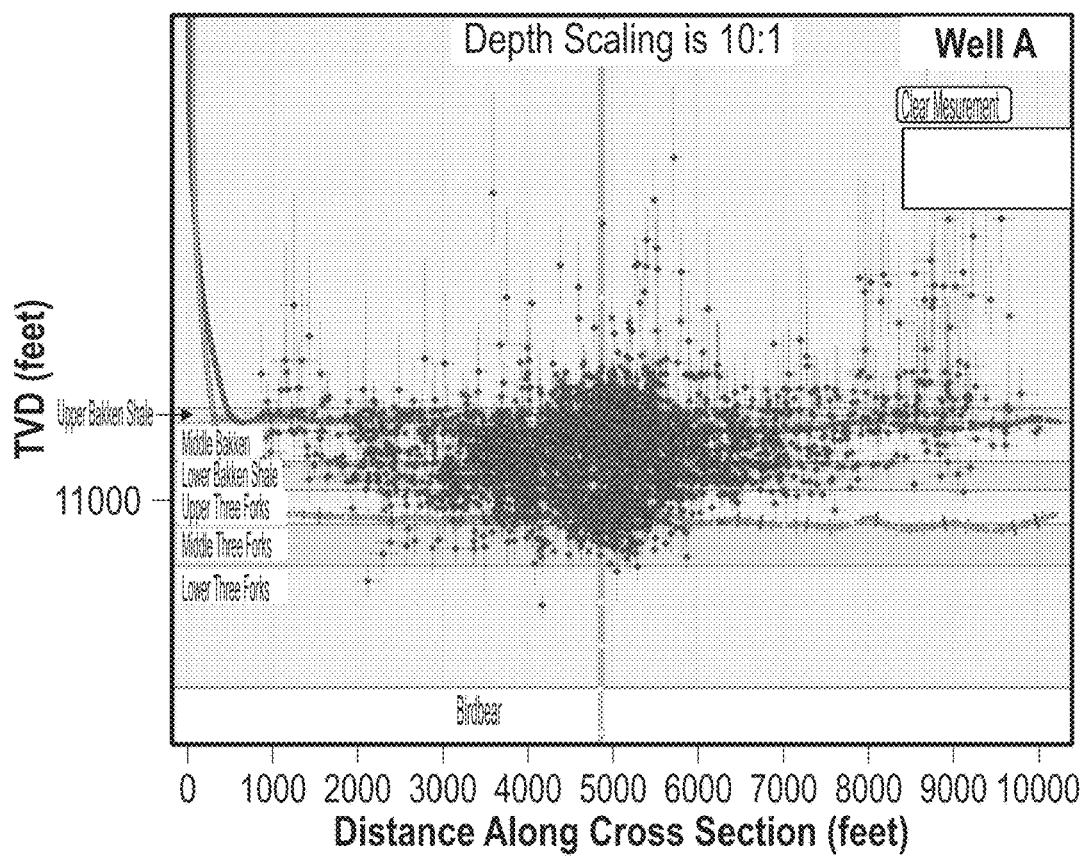
FIG. 12: Micro-seismic events observed in Well A (MB) and B (UTF). Location of vertical monitor well shown.
Figure 12:
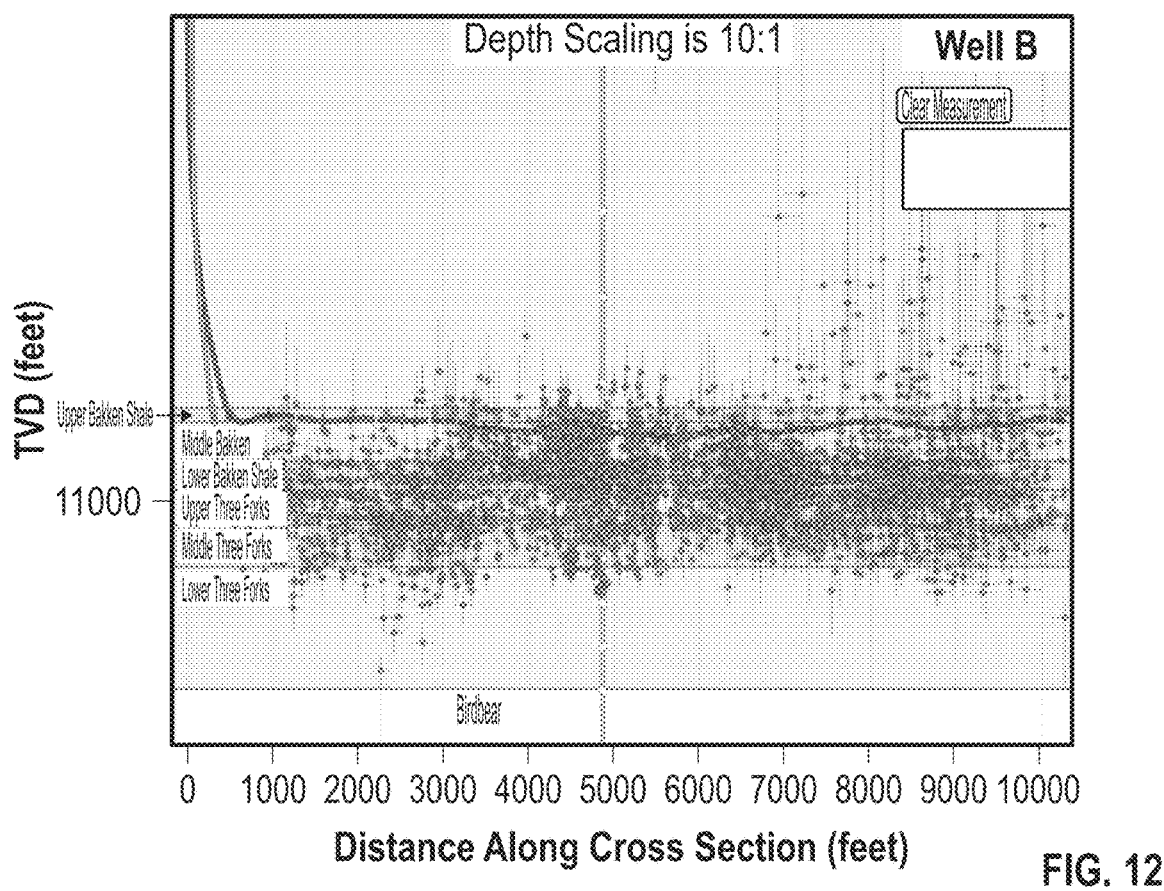
Figure 13:
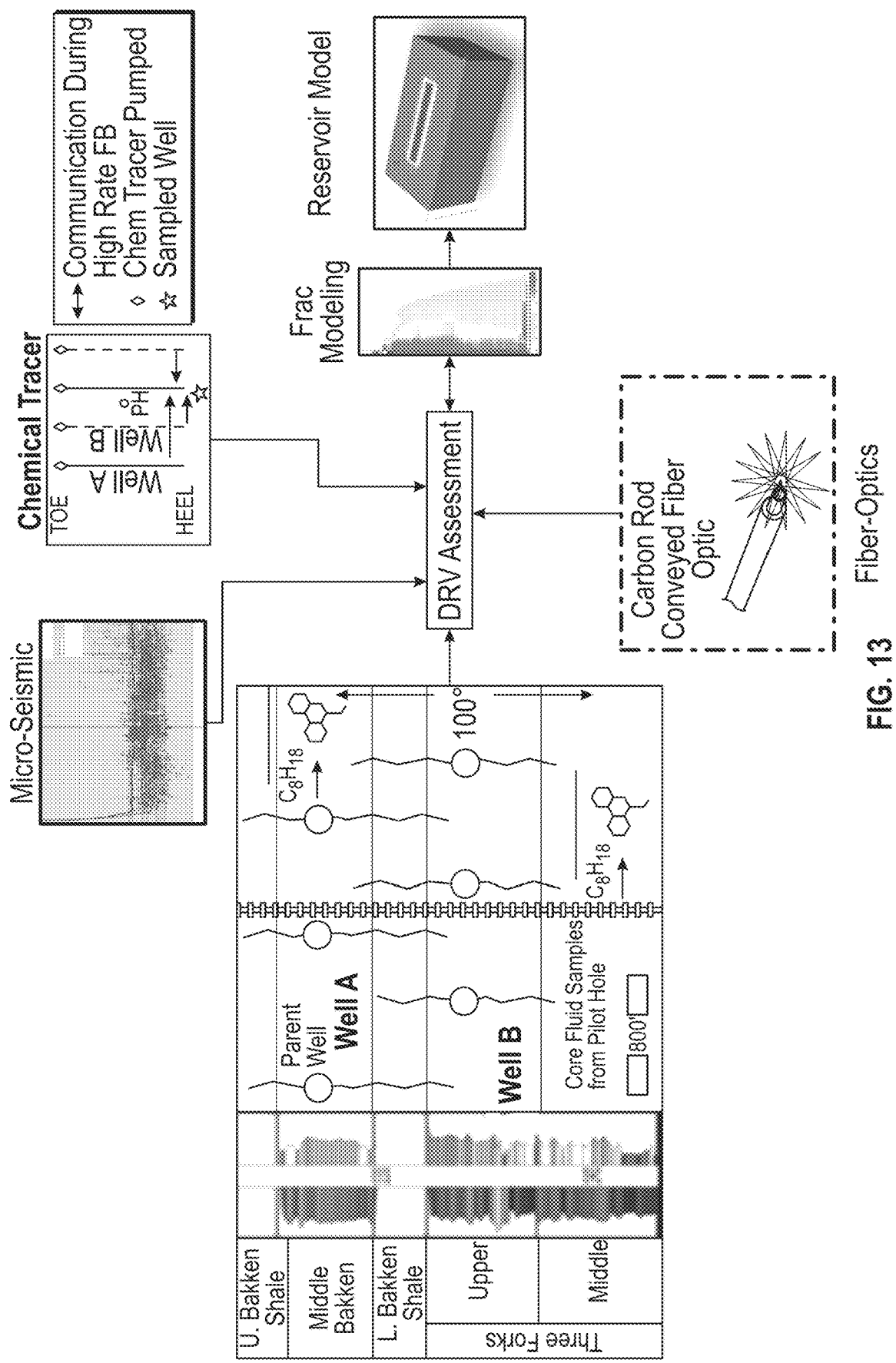
FIG. 13: The integrated workflow for DRV calibration using subsurface information.

The studied area is a data-rich, multi-well pilot where we also collected micro-seismic data (FIG. 12), chemical-tracer, as well as well interference tests. In the study area the DRV interpreted from our TLG results is more constrained than the SRV, as provided by the micro-seismic data. For Well A, the fracture height reflected by the micro-seismic data indicated the fractures reached up well beyond the UBS and down into the Middle and Lower TF, while TLG data indicated DRV was largely constrained between UBS and UTF. For Well B, microseismic showed the fracture growth up into the Lodgepole and down to the lower portion of the LTF, while the TLG provided DRV shows limited downward growth to MTF, which is consistent with production allocation indications of limited MTF contribution to production.

The mis-application of the SRV concept has been well discussed and largely explains the differences observed in the current study. SRV calculation is based on the spatial distribution of events, proximity to neighboring events, and event density. The relationship between SRV and fracture geometry is not completely understood, and microseismic events do not reveal any information in terms of fracture conductivity and connectivity to the wellbore. The SRV is indicative of the fracture height, length, and location, but the amount of the stimulated rock actually contributing to oil/gas/water production also hinges on many other factors including matrix permeability, proppant location, etc.

In comparison, since TLG is based on the produced fluid itself, the DRV calculated from the TLG data directly represents where the hydrocarbon and water is drained from as a result of combined effects of SRV, fracture and reservoir conductivity, proppant placement, etc. Therefore, it is understandable that the SRV is typically largely than the DRV as is observed in our case.

It is inherent that any diagnostic tool can only provide insights on what has happened, but cannot predict what will happen. Therefore, in order to predict the impact of key completion and development variables (landing zone, well spacing, job size, slick water vs. gel completion, etc.) to planning the field development, all information needs to be captured in a reservoir model. The TLG results are thus integrated with rock fracture modeling, rock and fluid properties and production information to calibrate the reservoir model and eventually explore the economic impact of assorted well spacing and stacking arrangements.

Figure 14:
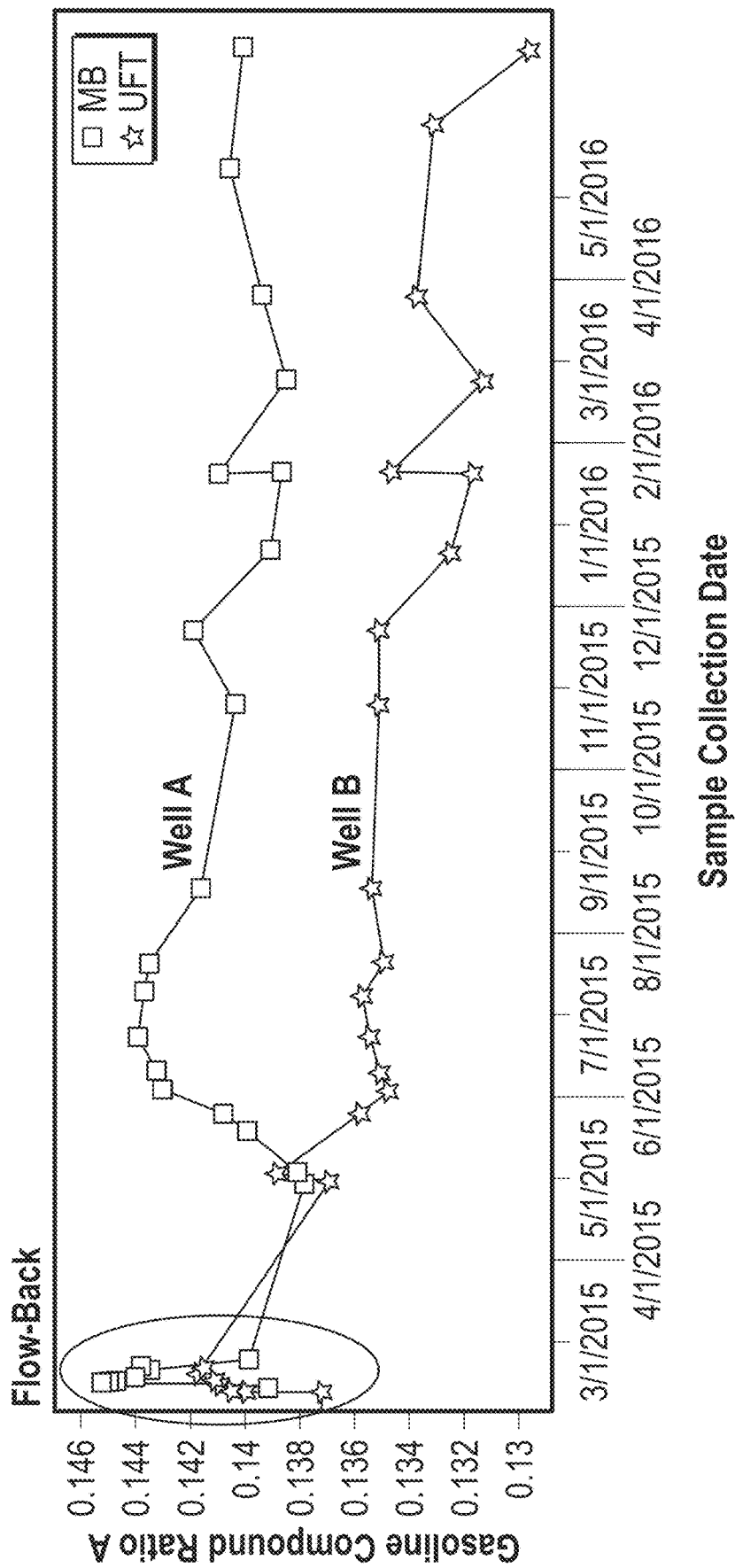
FIG. 14: An example of good separation between MB and TF wells using compounds in the gasoline range from GC.

FIG. 14. schematically demonstrates the integrated workflow of how TLG data were incorporated in the decision-making process for Bakken field development.

One limitation to the geochemistry-based methodology is the need to identify the distinct chemical signatures of end-members, which is not always available with proximal high quality core. The ability to extrapolate the end-members from core-extracted oil is limited also to a certain distance from the core. Thus, there may be a need to obtain better core samples, at some expense, to fully realize the value of this methodology. However, drilling cuttings may also provide useful data and are readily available at every rig site.

Figure 15:
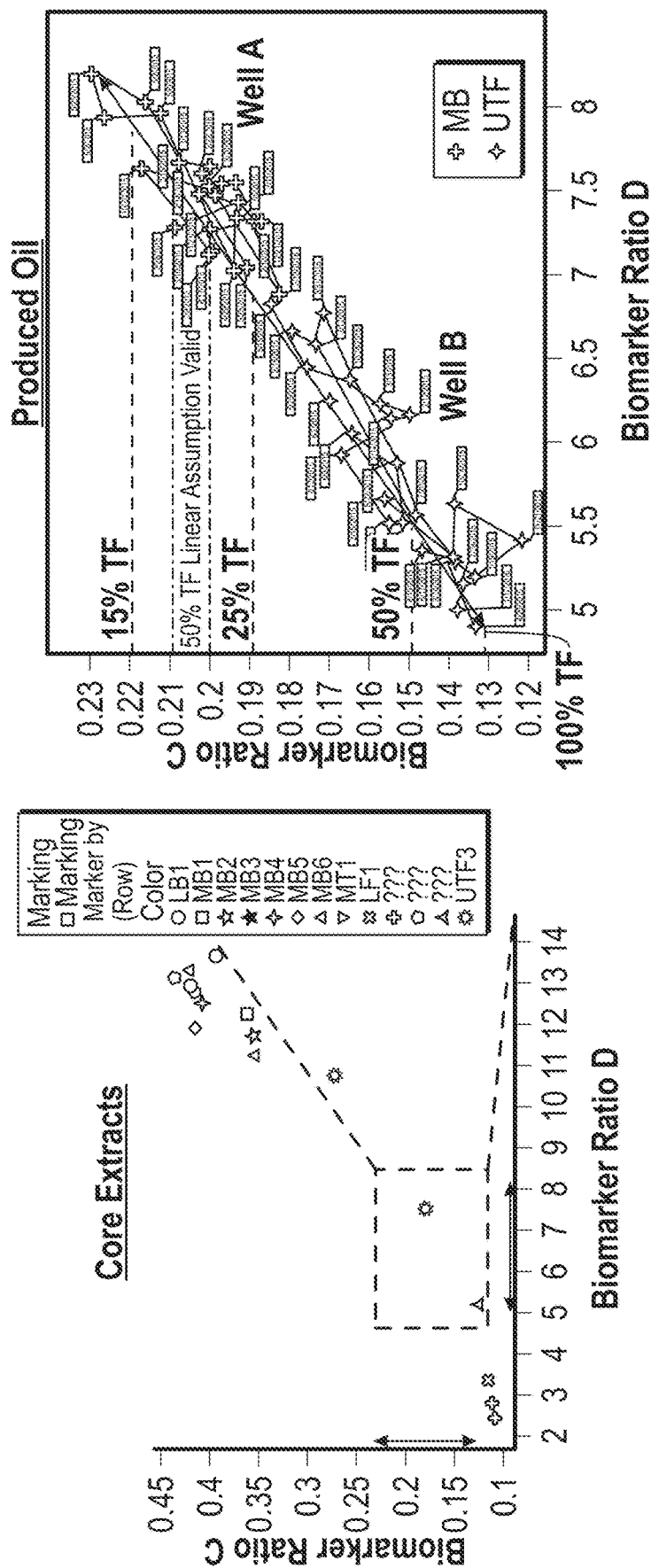
FIG. 15: An example of biomarker ratio shift from core extracts (left) to production oils (right), despite the range shift, they still carry valid qualitative information on the intervals. The TF mixing line for produced oil shown is for linear assumption where compounds in ratios are in nearly identical concentration and for non-linear using concentrations as observed; however, the unknown end member is subjectively set.

TLG data can also be utilized in a qualitative manner. This opens the potential for less expensive analytical tools (e.g. GC vs. GC-MS) and sometimes easier data processing. Qualitative methods can take advantage of the use of gasoline range compounds from GC (see example in FIG. 14) with high reproducibility, which are not present in core extracts. Many of the geochemical signals that are recorded and confirmed to carry valid zone separation information from core extracts can be confirmed in the produced oils, but due to difference in compound concentrations by zone and fractionation during production, are not useful for quantification (FIG. 15).

Figure 16:
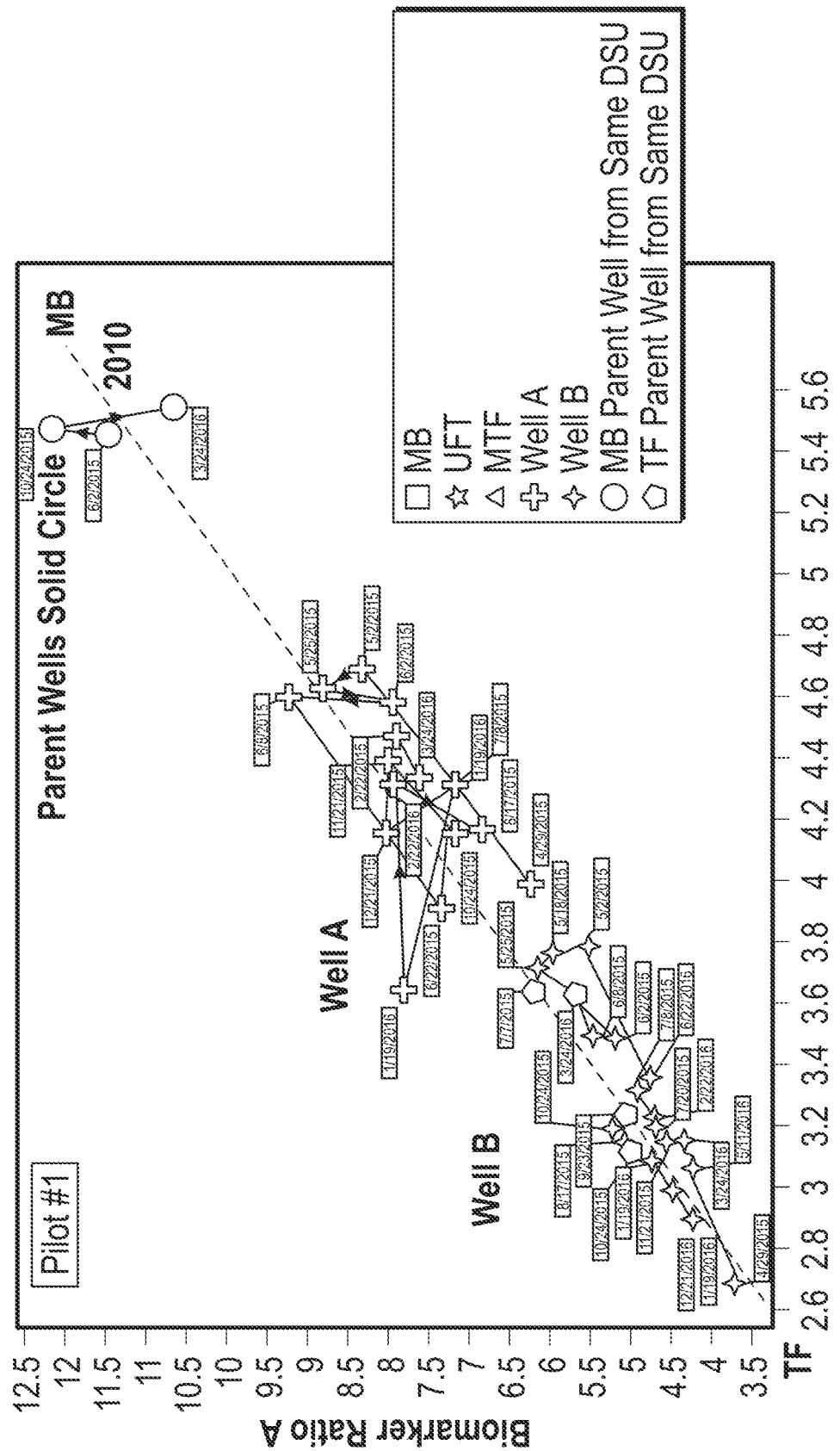
FIG. 16: Example of cross-plot of two diagnostic biomarker ratios that separate time series production for Well A and B and the two MB and TF parent wells. The MB parent well clearly separates from MB infill well (Well A) production while the TF parent well does not separate from its infill well (Well B). Note: MB parent well was completed in 2010 and the TF parent well was completed in 2013. Both Well A and B were completed in 2015. The data also indicate how older parent well drainage can be affected upon infill drilling.

An example of qualitative TLG monitoring is shown in FIG. 16. From quantitative analysis we know both MB and TF producers are mixtures due to vertical drainage. We do not know the exact 100% end-members on the plot, but a few items can be deduced from the data. The parent wells (wells drilled as the first wells in the area to hold lease, i.e., drilled into virgin rock) on production for 3-5 years prior to the in-fill wells have different responses. The parent MB well stays considerably away from MB in-fill, sampled before and after in-fill drilling and stimulation. From the prior discussion we know that the MB TLG average 55% MB (Table 2), therefor the parent MB likely represents predominately MB contribution. Interestingly, the TF parent well sampled after stimulation stays relatively grouped with the in-fill well. This suggests that the TF parent well continues to drain a mixed zone focused upward.

The TLG workflow and toolkit has been developed and continuously improved for applications in unconventional plays, first starting in the Barnett Shale gas play (Freeman et al. 2012). It has been successfully used in multiple liquid rich shale and tight hybrid plays across the North America including Barnett, Niobrara, Eagle Ford (Jweda et al. 2017), Bakken, and the Permian Basin, as well as in multiple areas and formations of the West Canada Sedimentary Basin.

We presented herein a novel approach using time-lapse geochemical fingerprinting in oil, gas and water to characterize the DRV and dynamic production contribution from each interval through time in an unconventional hybrid reservoir. The key challenge of end-member characterization in shales and other tight rocks was overcome by extracting oil from the core of corresponding intervals and statistically separating out repeatable zone-specific information.

As a new addition to the diagnostic toolkit for unconventional plays, TLG provides a cost-effective, non-invasive, and flexible (with different sampling frequency, different combination between oil, gas and water, etc.) option with a unique chemistry-based feature.

This method has been successfully applied in Bakken play where the key conclusions from this TLG application were as follows: 1) significant cross formation well communication (30~60%) was observed between stacked MB and UTF wells; 2) shale contribution remains low (within 5~10%) in both MB and UTF wells; 3) MTF contribution remains low in the UTF-completed well. These pieces of information show value in various field development decisions including well spacing and stacking, infill drilling, and well completion designs.

The present methods includes any of the following embodiments in any combination(s) of one or more thereof:

The following references are incorporated by reference in their entirety:

Baskin D. K., et al., 2014, Allocating the contribution of oil from the Eagle Ford Formation, the Buda Formation, and Austin Chalk to Commingled Production from Horizontal Wells in South Texas Using Geochemical Fingerprinting Technology; AAPG Annual Conventional May 19-22, 2013 Search and Discovery Article #41268

McCaffrey, et al., 1996, Using biomarkers to improve heavy oil reservoir management: An Example from Cymric Field, Kern County, California, AAPG Bull., v. 80,898-913.

McCaffrey, M. A., et al. (2012) Oil fingerprinting dramatically reduces production allocation costs. World Oil, March 2012, p 55-59.

McCaffrey, M. A., et al. (2011) Geochemical allocation of commingled oil production or commingled gas production. Society of Petroleum Engineers Paper Number 144618. p 1-19.

McCaffrey, M. A., D. K. Baskin, M. A. Beeunas, and B. A. Patterson, 2006, Reducing the Cost of Production Allocation by 95% Using a Geochemical Technique: Abstract, AAPG 2006 Annual Convention, Houston, Tex., Apr. 9-12, 2006.

SPE 162673: Rasdi F. et al., 2012, An investigation of vertical and lateral communication in an unconventional oil reservoir using geochemistry and reservoir simulation.

U.S. Pat. No. 9,074,465 Methods for allocating commingled oil production

U.S. Pat. No. 8,818,736 Allocating oil production from geochemical fingerprints

U.S. Pat. No. 8,360,143 Method of determining end member concentrations

U.S. Pat. No. 8,781,747 Method of determining parameters of a layered reservoir

SPE-184867-MS Ali Azad et al., Accelerating completions concept select in Unconventional Plays Using Diagnostics and Frac Modeling.

Jweda, J., et al. (2017). Optimizing field development strategy using time-lapse geochemistry in Eagle Ford. Unconventional Resources Technology Conference, Austin, Tex.

Laughland, M. M., D. E. Nelson, P. Wilson and E. Eastridge (2014). Uncharted Waters: What Can We Learn From Waters Produced From Horizontal Wells in the Permian Basin? Unconventional Resources Technology Conference, Denver, Colo., 25-27 Aug. 2014: 1946-1954.

Cipolla, C. (2015). How do we Optimize Hydraulic Fracturing in Shale Resource Plays? Learning from the Past and Predicting the Future, Society of Petroleum Engineers.

Cipolla, C. L., S. C. Maxwell and M. G. Mack (2012). Engineering Guide to the Application of Microseismic Interpretations, Society of Petroleum Engineers.

Freeman, C., G. J. Moridis, G. E. Michael and T. A. Blasingame (2012). Measurement, Modeling, and Diagnostics of Flowing Gas Composition Changes in Shale Gas Wells, Society of Petroleum Engineers.

Nouvelle et al., 2012, Novel Method of Production Back-Allocation Using Geochemical Fingerprinting SPE 160812

Nouvelle, 2011, US Patent 20130138360A1

Sandvik E. I. and Mercer J. N., 1990, Primary migration by bulk hydrocarbon flow, Org. Geochem., v.16, 83-89

Bowen, G. J. and B. Wilkinson (2002). "Spatial distribution of $\delta 18O$ in meteoric precipitation." *Geology* 30(4): 315-318.

Langman, J. B. (2015). "Spatial distribution of $\delta 2H$ and $\delta 18O$ values in the hydrologic cycle of the Nile Basin." *Journal of Arid Land* 7(2): 133-145.

Muehlenbachs, K. (1998). "The oxygen isotopic composition of the oceans, sediments and the seafloor." *Chemical Geology* 145(3-4): 263-273.

Capo, R. C., Stewart, B. W., Rowan, E. L., Kohl, C. A. K., Wall, A. J., Chapman, E. C., Hammack, R. W., and Schroeder, K. T., 2014. The strontium isotope evolution of Marcellus Formation produced waters, southwestern Pennsylvania. 126 57-63.

Chapman, E. C., Capo, R. C., Stewart, B. W., Kirby, C. S., and Hammack, R. W., 2012. Geochemical and strontium isotope characterization of produced waters from Marcellus Shale natural gas extraction. Environmental Science and Technology 46, 3545-3553.

Frost, C. D., and Toner, R. N., 2004. Strontium isotopic identification of water-rock interaction and ground water mixing. Ground Water, 42, 418-432.

Ebongue V. W., Jendrezejewsi N., Walgenwitz, Pineau F. and Javoy M., 2005, Cholorine isotope residual salt analysis: A new tool to investigate formation waters from core analyses. AAPG Bull., v. 89, no. 8, p. 1005-1018.

The invention claimed is:

1. A method of allocating production in a plurality of reservoirs, comprising:
    a) obtaining a plurality of rock samples from a plurality of zones of said one or more reservoir (s);
    b) chemically fingerprinting extracts from the plurality of rock samples;
    c) obtaining a plurality of produced oil, produced water and produced gas samples from a plurality of zones of one or more reservoir(s) over a period of time;
    d) chemically fingerprinting said plurality of samples to provide a plurality of oil fingerprints, a plurality of water fingerprints, and plurality of gas fingerprints;
    e) assigning a time and location identifier to one or more of said plurality of oil fingerprints, plurality of water fingerprints, and plurality of gas fingerprints; and
    f) allocating production from one or more wells in relation to the time and location of a plurality of fingerprints.

2. The method of claim 1, wherein said fingerprints comprise ratios of compounds that are generally constant between rock samples in a) and produced samples in b).

3. The method of claim 2, wherein said each compound in a ratio follows linear mixing rules.

4. The method of claim 2, wherein the fingerprints comprise ratios selected from gasoline compound ratios, biomarker ratios, gas compositional ratios, or water isotope ratios.

5. The method of claim 1, wherein raw fingerprinting data is fed into a macro that builds non-normalized (AB) and normalized (A/A+B) ratios of all possible compound ratios, and then ranks ratios using a square of Pearson correlation, wherein a ratio is selected for use in the method if i) said ratio is generally constant between rock samples in a) and produced samples in b), and ii) each compound in said ratio follows linear mixing rules, and iii) said ratio is clearly separate from drilling mud ratios.

6. The method of claim 1, wherein location includes depth and lateral placement (x, y and z axes).

7. The method of claim 1, wherein a reservoir map is generated in the form of tables including fingerprint data organized by location (x, y and z axes) and time.

8. The method of claim 1, wherein said chemically fingerprinting step uses GC, MS, GC-MS, FTICR-MS, TLC, 2D TLC, CE, HPLC, FTIR Spectrophotometry, XRF, AAS, ICP-MS, IC, NMR, GCxGC-TOFMS, SARA, CHNOS analysis, elemental analysis, or GC/IR-MS.

9. The method of claim 1, wherein said chemically fingerprinting step uses GC-MS.

10. The method of claim 1, wherein said water fingerprints include two or more isotopes selected from chlorine, bromide, strontium, water deuterium, water oxygen, sulfur, and iron.

11. The method of claim 1, wherein said gas fingerprints include two or more selected from carbon (13) level, sulfur (34) level, methane level, ethane level, propane level, butane level, pentane level, and $H_2S$ level.

12. The method of claim 1, wherein said oil fingerprints include API gravity, elemental composition, saturate levels, aromatic levels, resin levels, and asphaltene levels (SARA) fractions.

13. The method of claim 1, wherein said water fingerprints include carbon (13) level, sulfur (34) level, methane through pentane levels, $H_2S$ levels, metal levels, saturate levels, aromatic levels, resin levels, and asphaltene levels.

14. A method of optimizing well placement in a reservoir, comprising:
    a) obtaining a plurality of rock samples from a plurality of zones of said one or more reservoirs;
    b) chemically fingerprinting said plurality of rock samples to provide a plurality of rock fingerprints;
    c) grouping said plurality of zones into unique production zones by determining which fingerprints are unique;
    d) obtaining a plurality of produced oil, produced water and produced gas samples from a plurality of zones of one or more reservoir(s) over a period of time;
    e) chemically fingerprinting said plurality of samples to provide a plurality of oil fingerprints, a plurality of water fingerprints, plurality of gas fingerprints;
    f) assigning a time and location identifier to each of said plurality of oil fingerprints, plurality of water fingerprints, and plurality of gas fingerprints;
    g) determining which of said plurality of samples originate from which production zone by comparison to said unique fingerprints and determining a level of mixing according to the following equations:

$$p_i = \sum_{j=1}^{m} r_{i,j} w_j \quad (i = 1 \ldots n) \; n \geq m$$

$$\sum_{j=1}^{m} w_j = 1 \; 0 \leq w_j \leq 1$$

h) inputting data from (c) and (g) into a reservoir modeling program;
i) optimizing well placement using said reservoir modeling program; and
j) implementing said optimized well placement in said reservoir(s).

15. The method of claim 14, wherein said fingerprints comprise ratios of compounds that are generally constant between rock samples in a) and produced samples in b).

16. The method of claim 15, wherein said each compound in a ratio follows linear mixing rules.

17. The method of claim 15, wherein the ratios are selected from gasoline compound ratios, biomarker ratios, gas compositional ratios, water isotope and ratios.

18. The method of claim 14, wherein raw fingerprinting data is fed into a macro that builds non-normalized (AB) and normalized (A/A+B) ratios of all possible compound ratios, and then ranks ratios using a square of Pearson correlation, wherein a ratio is selected for use in the method if i) said ratio is generally constant between rock samples in a) and produced samples in b), and ii) each compound in said ratio follows linear mixing rules, and iii) said ratio is clearly separate from drilling mud ratios.

19. The method of claim 14, wherein location includes depth and lateral placement (x, y and z axes).

20. The method of claim 14, wherein a reservoir map is generated in the form of tables including fingerprint data organized by location (x, y and z axes) and time.

21. The method of claim 14, wherein said chemically fingerprinting step uses GC, MS, GC-MS, FTICR-MS, TLC, 2D TLC, CE, HPLC, FTIR Spectrophotometry, XRF, AAS, ICP-MS, IC, NMR, GCxGC-TOFMS, SARA, CHNOS analysis, elemental analysis, or GC/IR-MS.

22. The method of claim 14, wherein said chemically fingerprinting step uses GC-MS.

23. The method of claim 14, wherein said water fingerprints include two or more isotopes selected from chlorine, bromide, strontium, water deuterium, water oxygen, sulfur, and iron.

24. The method of claim 14, wherein said gas fingerprints include two or more selected from carbon (13) level, sulfur (34) level, methane level, ethane level, propane level, butane level, pentane level, and $H_2S$ level.

25. The method of claim 14, wherein said oil fingerprints include API gravity, elemental composition, saturate levels, aromatic levels, resin levels, and asphaltene levels (SARA) fractions.

26. The method of claim 14, wherein said water fingerprints include carbon (13) level, sulfur (34) level, methane through pentane levels, $H_2S$ levels, metal levels, saturate levels, aromatic levels, resin levels, and asphaltene levels.

27. A method of allocating production in an unconventional reservoir, comprising:
   a) obtaining a plurality of rock samples from a plurality of zones of said one or more unconventional reservoir(s);
   b) chemically fingerprinting said plurality of rock samples to provide a plurality of rock fingerprints;
   c) grouping said plurality of zones into unique production zones by determining which rock fingerprints are unique;
   d) obtaining a plurality of produced oil, produced water and optionally produced gas samples from a plurality of zones of one or more unconventional reservoir(s) over a period of time;
   e) chemically fingerprinting said plurality of samples to provide a plurality of oil fingerprints, a plurality of water fingerprints, and optionally a plurality of gas fingerprints;
   i) wherein all fingerprint data is simplified by generating ratios of all possible compound ratios, and selecting a ratio for use in the method if i) said ratio is generally constant between a) and d), and ii) each compound in said ratio follows linear mixing rules, and iii) said ratio is clearly separate from ratios obtained from drilling mud fingerprints;
   f) determining which portion of said plurality of samples originate from which production zone(s) by comparison to said unique fingerprints and determining a level of mixing according to linear algebraic equations,
      thereby determining which unique zone contributes to production of oil, gas and water samples and how much.

28. The method of claim 27, wherein raw fingerprinting data is fed into a macro that builds non-normalized (AB) and normalized (A/A+B) ratios of all possible compound ratios, and then ranks ratios using a square of Pearson correlation, wherein a ratio is selected for use in the method if i) said ratio is generally constant between rock samples in a) and produced samples in b), and ii) each compound in said ratio follows linear mixing rules, and iii) said ratio is clearly separate from drilling mud ratios.

29. The method of claim 27, wherein location includes depth and lateral placement (x, y and z axes).

30. The method of claim 27, wherein a reservoir map is generated in the form of tables including fingerprint data organized by location (x, y and z axes) and time.

31. The method of claim 27, wherein said chemically fingerprinting step uses GC, MS, GC-MS, FTICR-MS, TLC, 2D TLC, CE, HPLC, FTIR Spectrophotometry, XRF, AAS, ICP-MS, IC, NMR, GCxGC-TOFMS, SARA, CHNOS analysis, elemental analysis, or GC/IR-MS..

32. The method of claim 27, wherein said chemically fingerprinting step uses GC-MS.

33. The method of claim 27, wherein the ratio is selected from gasoline compound ratios, biomarker ratios, gas compositional ratios, and water isotope ratios.

34. The method of claim 27, wherein said water fingerprints include two or more isotopes selected from chlorine, bromide, strontium, water deuterium, water oxygen, sulfur, and iron.

35. The method of claim 27, wherein said gas fingerprints include two or more selected from carbon (13) level, sulfur (34) level, methane level, ethane level, propane level, butane level, pentane level, and $H_2S$ level.

36. The method of claim 27, wherein said oil fingerprints include API gravity, elemental composition, saturate levels, aromatic levels, resin levels, and asphaltene levels (SARA) fractions.

37. The method of claim 27, wherein said water fingerprints include carbon (13) level, sulfur (34) level, methane through pentane levels, $H_2S$ levels, metal levels, saturate levels, aromatic levels, resin levels, and asphaltene levels.

* * * * *